(12) United States Patent
Bigg et al.

(10) Patent No.: US 7,015,213 B1
(45) Date of Patent: Mar. 21, 2006

(54) USE OF DIAZEPINES FOR PREPARING MEDICINES FOR TREATING PATHOLOGICAL CONDITIONS OR DISEASES INVOLVING ONE OF THE GROWTH HORMONE RELEASE INHIBITING FACTOR RECEPTORS

(75) Inventors: Dennis Bigg, Gif-sur-Yvette (FR); Anne-Marie Liberatore, Auffargis (FR); Jacques Pommier, Colombes (FR); John Taylor, Upton, MA (US)

(73) Assignee: Societe de Conseils de Recherches et d'Applications Scientifiques (S.C.R.A.S.), (FR)

( * ) Notice: Subject to any disclaimer, the term of this patent is extended or adjusted under 35 U.S.C. 154(b) by 0 days.

(21) Appl. No.: 09/701,893

(22) PCT Filed: Jun. 15, 1999

(86) PCT No.: PCT/FR99/01422

§ 371 (c)(1),
(2), (4) Date: Dec. 1, 2000

(87) PCT Pub. No.: WO99/65917

PCT Pub. Date: Dec. 23, 1999

(30) Foreign Application Priority Data

Jun. 15, 1998 (FR) .................................. 98 07509

(51) Int. Cl.
| | | |
|---|---|---|
| A61K 31/55 | (2006.01) | |
| C07D 243/22 | (2006.01) | |
| C07D 243/24 | (2006.01) | |
| C07D 495/04 | (2006.01) | |
| C07D 495/14 | (2006.01) | |

(52) U.S. Cl. ...................................... 514/219; 540/555
(58) Field of Classification Search ................ 514/219; 540/555
See application file for complete search history.

(56) References Cited

FOREIGN PATENT DOCUMENTS

| EP | 367 110 | * 5/1990 |
|---|---|---|
| EP | 503 471 | * 9/1992 |
| EP | 0638560 | 2/1995 |
| FR | 2 660 311 | * 10/1991 |

OTHER PUBLICATIONS

CAPLUS printout of Prunonosa et al., Determnation of the Anti-Platelet-Activating Factor BN-50727 and Metabolites in Human Urine by High-Performance Liquid Chromatography Using Solid-Phase Extraction, J. Chromatogr., B: Biomed. Appl., vol. 677, No. 2, pp. 388-392, 1996.*

CAPLUS printout of Girault et al., Simultaneous Quantitative Measurement of a New Platelet Activating Factor Antagonist (BN 50730) and its Two Main Metabolites in Human Plasma and Urine by LC-MS, Chromatographia, vol. 39, No. 3-4, pp. 228-238, 1994.*

CAPLUS printout of Miyazawa et al., Structure-Activity Studies on Triazolothienodiazepine Derivatives as Platelet-Activating Factor Antagonists, Chem. Pharm. Bull., vol. 39, No. 12, pp. 3215-3220, 1991.*

Yang, L., Non-Peptide Somatostatin Receptor Ligands, Annual Reports In Medicinal Chemistry, vol. 34, pp. 209-218, 1999.*

Doly et al, "Prevention . . . BN 50730", Ophthalmic Research, vol. 25, 1993, pp. 314-318.

Rabinovici et al, "Platelet . . . Antagonist", Journal of Pharmacology and Experimental Therapeutics, vol. 225, No. 1, 1990, pp. 256-263.

* cited by examiner

Primary Examiner—Brenda Coleman
(74) Attorney, Agent, or Firm—Charles A. Muserlian

(57) ABSTRACT

The invention concerns the use of pyrido-thieno-triazolo-diazepins for preparing a medicine for treating pathological conditions or diseases involving one of the growth hormone release inhibiting factor receptors. The invention also concerns novel pyrido-thieno-triazolo-diazepins and therapeutic compositions containing them.

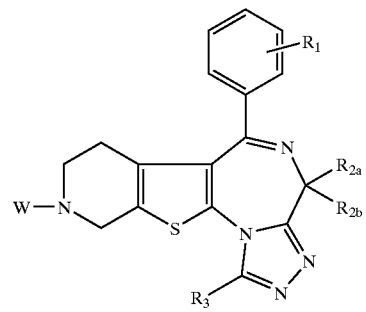

6 Claims, No Drawings

USE OF DIAZEPINES FOR PREPARING MEDICINES FOR TREATING PATHOLOGICAL CONDITIONS OR DISEASES INVOLVING ONE OF THE GROWTH HORMONE RELEASE INHIBITING FACTOR RECEPTORS

This application is a 371 of PCT/FR99/01422 filed Jun. 15, 1999.

The present invention relates to the use of pyrido-thieno-triazolo-diazepines for the preparation of a medicament intended to treat the pathological states or the diseases in which one (or more) of the somatostatin receptors are involved. The invention also relates to new pyrido-thieno-triazolo-diazepins and the therapeutic compositions containing them.

Somatostatin (SST) is a cyclic tetradecapeptide which was isolated for the first time from the hypothalamus as a substance which inhibits the growth hormone (Brazeau P. et al., *Science* 1973, 179, 77–79). It also operates as a neurotransmitter in the brain (Reisine T. et al., *Neuroscience* 1995, 67, 777–790; Reisine et al., *Endocrinology* 1995, 16, 427–442). Molecular cloning has allowed it to be shown that the bioactivity of somatostatin depends directly on a family of five receptors.

Among the pathological disorders associated with somatostatin (Moreau J. P. et al., Life Sciences 1987, 40, 419; Harris A. G. et al., The European Journal of Medicine, 1993, 2, 97–105), there can be mentioned for example: acromegalia, hypophyseal adenomas, Cushing's disease, gonadotrophinomas and prolactinomas, catabolic side-effects of glucocorticoids, insulin dependent diabetes, diabetic retinopathy, diabetic nephropathy, hyperthyroidism, gigantism, endocrinic gastroenteropancreatic tumors including carcinoid syndrome, VIPoma, insulinoma, nesidioblastoma, hyperinsulinemia, glucagonoma, gastrinoma and Zollinger-Ellison's syndrome, GRFoma as well as acute bleeding of the esophageal varices, gastroesophageal reflux, gastroduodenal reflux, pancreatitis, enterocutaneous and pancreatic fistule but also diarrheas, refractory diarrheas of acquired immunodeficiency syndrome, chronic secretary diarrhea, diarrhea associated with irritable bowel syndrome, disorders linked with gastrin releasing peptide, secondary pathologies with intestinal grafts, portal hypertension as well as hemorrhages of the varices in patients with cirrhosis, gastro-intestinal hemorrhage, hemorrhage of the gastroduodenal ulcer, Crohn's disease, systemic scleroses, dumping syndrome, small intestine syndrome, hypotension, scleroderma and medullar thyroid carcinoma, illnesses linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and other therapeutic fields such as, for example, cephaleas including cephalea associated with hypophyseal tumors, pain, panic attacks, chemotherapy, cicatrization of wounds, renal insufficiency resulting from delayed development, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukemia, meningioma, cancerous cachexia, inhibition of H pylori, psoriasis, as well as Alzheimer's disease. Osteoporosis can also be mentioned.

In the Patent FR 2645153, the Applicant described diazepines which have an anti-PAF activity. The Applicant found that these products and products related to these compounds have an affinity and a selectivity for the somatostatin receptors. As somatostatin and its peptide analogues often have a poor bioavailability by oral route and a low selectivity (Robinson, C., Drugs of the Future, 1994, 19, 992; Reubi, J. C. et al., TIPS, 1995, 16, 110), said compounds, non-peptide agonists or antagonists of somatostatin, can be advantageously used to treat the pathological states or the diseases as presented above and in which one (or more) somatostatin receptors are involved. Preferably, these compounds can be used for the treatment of acromegalia, hypophyseal adenomas or endocrine gastroenteropancreatic tumors including carcinoid syndrome.

Therefore a subject of the invention is the use of a compound of general formula I

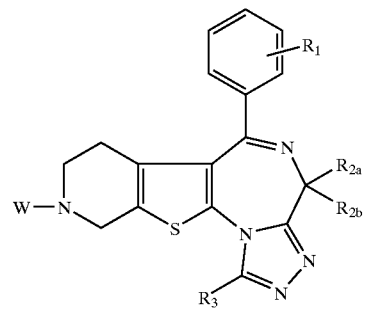

in which
W represents the hydrogen atom or a radical of formula R—X—C(Y)—;
R represents an aryl or heteroaryl radical, the aryl and heteroaryl radicals being optionally substituted;
X represents a radical of formula —$(CH_2)_n$—Z in which Z represents a covalent bond, NH, O or S and n an integer of 0 to 2;
Y represents O or S;
$R_1$ represents one or more groups, identical or different, chosen from: the hydrogen atom, the hydroxy, halo radical, a lower alkyl, lower alkoxy or radical;
$R_{2a}$ and $R_{2b}$ represent, independently, the hydrogen atom; a lower alkyl, lower alkenyl or lowr alkynyl radical, the alkyl, alkenyl and alkynyl radicals being optionally substituted; or an $R_{21}Z_{21}$-radical in which $Z_{21}$ represents O, C(O), OC(O), S, and $R_{21}$ represents the hydrogen atom, a lower alkyl, aryl or arylalkyl radical;
$R_3$ represents the hydrogen atom, the halo, nitro or cyano radical, an alkyl radical with 1 to 10 carbon atoms, lowr alkenyl, lower alkynyl, cycloalkyl, cycloalkylalkyl, aryl, arylalkyl, lower aryloxyalkyl, heteroaryl or heteroarylalkyl, the alkyl, alkenyl, alkynyl, cycloalkyl, aryl and heteroaryl radicals being optionally substituted; or an $R_{31}Z_{31}$-radical in which $Z_{31}$ represents O, C(O), OC(O), S, and $R_{31}$ represents the hydrogen atom, a lower alkyl, aryl or lower arylalkyl radical;

or a salt of this product (when the molecule contains a basic group), for the preparation of a medicament intended to treat the pathological states or the diseases in which one (or more) of the somatostatin receptors is involved.

A more particular subject of the invention is the use, for the preparation of a medicament intended to treat the pathological states or the diseases in which one (or more) of the somatostatin receptors is involved, of a compound of general formula I as defined above in which W represents the hydrogen atom or a radical of formula R—X—C(Y)—;

R represents an aryl or heteroaryl radical, the aryl and heteroaryl radical being optionally substituted by one or more identical or different substituents, chosen from the following radicals: lower alkyl, lower alkoxy, lowr alkylthio, lower alkoxy carbonyl, lower alkyl sulphonyl, halo, trifluoromethyl, trifluoromethyloxy, hydroxy, nitro, cyano, aryl, aryloxy, cycloalkyl or heterocycloalkyl;

$R_1$ represents one or more identical or different groups, chosen from: the hydrogen atom, the hydroxy radical, halo, a lower alkyl radical, lower alkoxy, the alkyl and alkoxy radicals being optionally substituted by one or more identical or different radicals chosen from the following radicals: trifluoromethyl, lower alkoxy, amino, lower alkyl amino and lower dialkyl amino;

$R_{2a}$ and $R_{2b}$ represent, independently:
  the hydrogen atom;
  a lower alkyl, lower alkenyl or lower alkynyl radical, the alkyl, alkenyl and alkynyl radicals being optionally substituted by one more identical or different radicals, chosen from:
    halo; an —$NR_{22}R_{23}$ radical in which $R_{22}$ and $R_{23}$ represent, independently, the hydrogen atom, a lower alkyl, cycloalkyl, cycloalkylalkyl, aryl, arylalkyl, heteroaryl, heteroarylalkyl, alkylsulphonyl, cycloalkylsulphonyl, arylsulphonyl, lower alkoxy carbonyl, aryloxycarbonyl, alkylcarbonyl, arylcarbonyl or cycloalkylcarbonyl radical; or a —$Z_{22}R_{24}$ radical in which $Z_{22}$ represents O, S, C(O) OC(O) and $R_{24}$ represents a hydrogen atom, a lower alkyl, cycloalkyl, cycloalkylalkyl, aryl, arylalkyl, heteroaryl, heteroarylalkyl, alkylsulphonyl, cycloalkylsulphonyl or arylsulphonyl radical;
    an $R_{21}Z_{21}$-radical in which $Z_{21}$ represents O, C(O), OC(O), S, and $R_{21}$ represents the hydrogen atom, a lower alkyl, aryl, aryl or arylalkyl radical;

$R_3$ represents:
  the hydrogen atom, the halo, nitro or cyano radical;
  an alkyl radical with 1 to 10 carbon atoms, lower alkenyl, lower alkynyl, cycloalkyl, cycloalkylalkyl, aryl, lower arylalkyl, lowr aryloxyalkyl, heteroaryl or lower heteroarylalkyl, the alkyl, alkenyl, alkynyl, cycloalkyl, aryl and heteroaryl radicals being optionally substituted by one or more identical or different radicals chosen from:
    halo; aryl; —$NR_{32}R_{33}$ in which either $R_{32}$ and $R_{33}$ represent, independently, the hydrogen atom, a lower alkyl, arylalkyl or alkylcarbonyl radical, or $R_{32}$ and $R_{33}$ form, with the nitrogen atom to which they are attached, a heterocycloalkyl; or —$Z_{32}$—$Z_{34}$ in which $Z_{32}$ represents O, C(O), OC(O), S, S(O) or $SO_2$ and $R_{34}$ represents the hydrogen atom, a lower alkyl, aryl or lower alkylalkyl radical;
  a —$Z_{31}R_{31}$ radical in which $Z_{31}$ represents O, C(O), OC(O), S, and $R_{31}$ represents the hydrogen atom, a lower alkyl, aryl or arylalkyl radical.

In the definitions indicated above, the expression halo represents the fluoro, chloro, bromo or iodo radical, preferably chloro, fluoro or bromo. The expression lower alkyl preferably represents a linear or branched alkyl radical having 1 to 6 carbon atoms, and in particular an alkyl radical having 1 to 4 carbon atoms such as the methyl, ethyl, propyl, isopropyl, butyl, isobutyl, sec-butyl and tert-butyl radicals, but can also represent a pentyl, isopentyl, hexyl or isohexyl radical. Among the alkyl radicals containing 1 to 10 carbon atoms, the lower alkyls as defined above can be mentioned but also the heptyl, octyl, nonyl or decyl radicals.

The lower alkoxy radicals can correspond to the alkyl radicals indicated above such as for example the methoxy, ethoxy, propyloxy or isopropyloxy radicals but also linear, secondary or tertiary butoxy. The term lower alkylthio preferably designates the radicals in which the alkyl radical is as defined above such as for example methylthio, ethylthio.

The expression lower alkenyl preferably represents a linear or branched alkenyl radical having 1 to 6 carbon atoms, such as for example vinyl, allyl, propenyl, butenyl or pentenyl. The terme lower alkynyl preferably represents a linear or branched alkynyl containing 1 to 6 carbon atoms, and preferably an ethynyl, propargyl, butynyl or pentynyl radical.

The terme cycloalkyl preferably designates the cyclopropyl, cyclobutyl, cyclopentyl or cyclohexyl rings. The expression heterocycloalkyl designates a saturated cycloalkyl containing 2 to 7 carbon atoms and at least one heteroatom. This radical can contain several identical or different heteroatoms. Preferably, the heteroatoms are chosen from oxygen, sulphur or nitrogen. As examples of heterocycloalkyl, there can be mentioned the pyrrolidine, imidazolidine, pyrrazolidine, isothiazolidine, thiazolidine, isoxazolidine, oxazolidine ring or a ring of formula

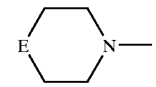

in which E represents $CH_2$, O or $R_4N$ in which $R_4$ represents hydrogen, a lower alkyl, arylalkyl, arylsulphonyl, optionally substituted aryl radical, thus being able to represent for example the piperidine, piperazine or morpholine ring.

The expression aryl represents an aromatic radical, constituted by a ring or condensed rings, such as for example the phenyl or naphthyl radical. The term aryloxy preferably designates the radicals in which the aryl radical is as defined above such as for example the phenoxy radical. The expression heteroaryl designates an aromatic radical, constituted by a ring or condensed rings, with at least one ring containing one or more identical or different heteroatoms chosen from sulphur, nitrogen or oxygen. As an example of a heteroaryl radical, thienyl, furyl, pyrrolyl, imidazolyl, pyrazolyl, isothiazolyl, thiazolyl, isoxazolyl, oxazolyl, pyridyl, pyrazinyl, pyrimidiyl, benzothienyl, benzofuryl and indolyl radicals can be mentioned.

The lower arylalkyl radicals designate the radicals in which respectively the aryl and lower alkyl radicals are as defined above such as for example benzyl, phenethyl or naphthylmethyl. The lower heteroarylalkyl radicals designate the radicals in which respectively the heteroaryl and lower alkyl radicals are as defined above such as for example indolylmethyl, thienylmethyl, furylmethyl. The term aryloxyalkyl designates the radicals in which respectively the aryloxy and lower alkyl radicals are as defined above.

The terms lower alkyl amino and lower dialkyl amino preferably designate the radicals in which the alkyl radicals are as defined above, such as for example methylamino, ethylamino, dimethylamino, diethylamino or (methyl)(ethyl)amino.

The terms alkylsulphonyl, cycloalkylsulphonyl, arylsulphonyl and arylalkylsulphonyl preferably designate the radicals in which respectively the alkyl, cycloalkyl and aryl radicals are as defined above. Similarly, the terms alkylcarbonyl, alkoxycarbonyl, arylcarbonyl, aryloxycarbonyl preferably designate the radicals in which respectively the alkyl, alkoxy, aryl and aryloxy radicals are as defined above.

When the products of formula I contain a basic group, they can form addition salts with acids, in particular pharmacologically acceptable acids.

According to the definition of the variable groups, a compound of formula I as defined above can have one or more asymmetrical carbons. The invention relates to the use of the compounds of formula I as defined above, which compounds can be found in racemic, enantiometric or diastereoisomeric form.

A more particular subject of the invention is the use, for the preparation of a medicament intended to treat the pathological states or the diseases in which one (or more) of the somatostatin receptors are involved, of a compound of general formula I as defined above in which
  W represents the hydrogen atom or a radical of formula R—X—C(Y)—;
  R represents an aryl or heteroaryl radical, the aryl and heteroaryl radicals being optionally substituted by one or more identical or different substituents, chosen from the following radicals: lower alkyl, lower alkoxy, lowr alkylthio, lower alkoxy carbonyl, lower alkyl sulphonyl, halo, trifluoromethyl, trifluoromethyloxy, hydroxy, nitro, cyano, aryl, aryloxy or heterocycloalkyl;
  $R_1$ represents one or more identical or different groups, chosen from: the hydrogen atom, a halo, lower alkyl or lower alkoxy radical;
  $R_{2a}$ and $R_{2b}$ represent, independently the hydrogen atom or a lower alkyl radical;
  $R_3$ represents the hydrogen atom; an alkyl radical with 1 to 10 carbon atoms, cycloalkylalkyl, aryl, lower, lower arylalkyl or lower heteroarylalkyl, the alkyl, cycloalkyl, aryl and heteroaryl radicals being optionally substituted by one or more identical or different radicals chosen from:
    aryl; —$NR_{32}R_{33}$ in which either $R_{32}$ and $R_{33}$ represent, independently, the hydrogen atom or a lower alkyl radical; or —$Z_{32}$—$Z_{34}$ in which $Z_{32}$ represents O and $R_{34}$ represents the hydrogen atom or a lower alkyl radical.

A more particular subject of the invention is the use, for the preparation of a medicament intended to treat the pathological states of the diseases in which one (or more) of the somatostatin receptors is involved, of a compound of formula I as defined above, characterized in that
  W represents the hydrogen atom or a radical of formula R—X—C(Y)—;
  R represents the phenyl, naphthyl, indolyl or pyridyl radical, these radicals being optionally substituted by one or more identical or different substituents chosen from the following radicals: methyl, ethyl, propyl, isopropyl, butyl, ter-butyl, methoxy, ethoxy, methylthio, ethylthio, methoxycarbonyl, ethoxycarbonyl, methylsulphonyl, ethylsulphonyl, chloro, fluoro, bromo, trifluoromethyl, trifluoromethyloxy, hydroxy, nitro, cyano, phenyl, phenoxy or morpholino;
  X represents $CH_2$, $C_2H_4$, $CH_2NH$, NH, O, S or a covalent bond;
  Y represents O or S;
  $R_1$ represents one or more identical or different groups, chosen from: the hydrogen atom, a chloro, methyl or methoxy radical;
  $R_{2a}$ and $R_{2b}$ represent, independently, the hydrogen atom or a methyl radical;
  $R_3$ represents the hydrogen atom, methyl, ethyl, propyl, butyl, pentyl, hexyl, heptyl, methoxyethyl, ethoxyethyl, dimethylaminoethyl, cyclohexylmethyl, phenyl, diphenyl, benzyl optionally substituted by the hydroxy or methoxy, phenethyl, naphthylmethyl or indolylmethyl radical.

More particularly, a subject of the invention is the use, for the preparation of a medicament intended to treat the pathological states or the diseases in which one (or more) of the somatostatin receptors is involved, of the compounds described hereafter in the examples, in particular the products corresponding to the following formulae:
1-butyl-6-(2-chlorophenyl)-7,8,9,10-tetrahydro-4H-pyrido[4',3';4,5]thieno[3,2-f][1,2,4]triazolo[4,3-a][1,4]diazepine;
1-benzyl-6-(2-chlorophenyl)-7,8,9,10-tetrahydro-4H-pyrido[4',3';4,5]thieno[3,2-f][1,2,4]triazolo[4,3-a][1,4]diazepine;
1-methyl-6-(2-chlorophenyl)-7,8,9,10-tetrahydro-4H-pyrido[4',3';4,5]thieno[3,2-f][1,2,4]triazolo[4,3-a][1,4]diazepine;
6-(2-chlorophenyl)-7,8,9,10-tetrahydro-4H-pyrido[4',3';4,5]thieno[3,2-f][1,2,4]triazolo[4,3-a][1,4]diazepine;
1-ethyl-6-(2-chlorophenyl)-7,8,9,10-tetrahydro-4H-pyrido[4',3';4,5]thieno[3,2-f][1,2,4]triazolo[4,3-a][1,4]diazepine;
1-propyl-6-(2-chlorophenyl)-7,8,9,10-tetrahydro-4H-pyrido[4',3';4,5]thieno[3,2-f][1,2,4]triazolo[4,3-a][1,4]diazepine;
1-phenyl-6-(2-chlorophenyl)-7,8,9,10-tetrahydro-4H-pyrido[4',3';4,5]thieno[3,2-f][1,2,4]triazolo[4,3-a][1,4]diazepine;
1-pentyl-6-(2-chlorophenyl)-7,8,9,10-tetrahydro-4H-pyrido[4',3';4,5]thieno[3,2-f][1,2,4]triazolo[4,3-a][1,4]diazepine;
1-hexyl-6-(2-chlorophenyl)-7,8,9,10-tetrahydro-4H-pyrido[4',3';4,5]thieno[3,2-f][1,2,4]triazolo[4,3-a][1,4]diazepine;
1-(4-hydroxybenzyl)-6-(2-chlorophenyl)-7,8,9,10-tetrahydro-4H-pyrido[4',3';4,5]thieno[3,2-f][1,2,4]triazolo[4,3-a][1,4]diazepine;
1-(4-methoxybenzyl)-6-(2-chlorophenyl)-7,8,9,10-tetrahydro-4H-pyrido[4',3';4,5]thieno[3,2-f][1,2,4]triazolo[4,3-a][1,4]diazepine;
1-(1-naphthyl-methyl)-6-(2-chlorophenyl)-7,8,9,10-tetrahydro-4H-pyrido[4',3';4,5]thieno[3,2-f][1,2,4]triazolo[4,3-a][1,4]diazepine;
1-(3-indolyl-methyl)-6-(2-chlorophenyl)-7,8,9,10-tetrahydro-4H-pyrido[4',3';4,5]thieno[3,2-f][1,2,4]triazolo[4,3-a][1,4]diazepine;
1-phenethyl-6-(2-chlorophenyl)-7,8,9,10-tetrahydro-4H-pyrido[4',3';4,5]thieno[3,2-f][1,2,4]triazolo[4,3-a][1,4]diazepine;
1-diphenyl-6-(2-chlorophenyl)-7,8,9,10-tetrahydro-4H-pyrido[4',3';4,5]thieno[3,2-f][1,2,4]triazolo[4,3-a][1,4]diazepine;
1-ethoxyethyl-6-(2-chlorophenyl)-7,8,9,10-tetrahydro-4H-pyrido[4',3';4,5]thieno[3,2-f][1,2,4]triazolo[4,3-a][1,4]diazepine;

1-cyclohexylmethyl-6-(2-chlorophenyl)-7,8,9,10-tetrahydro-4H-pyrido[4',3';4,5]thieno[3,2-f][1,2,4]triazolo[4,3-a][1,4]diazepine;
1-(3-hydroxybenzyl)-6-(2-chlorophenyl)-7,8,9,10-tetrahydro-4H-pyrido[4',3';4,5]thieno[3,2-f][1,2,4]triazolo[4,3-a][1,4]diazepine;
1-(dimethylaminoethyl)-6-(2-chlorophenyl)-7,8,9,10-tetrahydro-4H-pyrido[4',3';4,5]thieno[3,2-f][1,2,4]triazolo[4,3-a][1,4]diazepine;
1-methyl-6-phenyl-7,8,9,10-tetrahydro-4H-pyrido[4',3';4,5]thieno[3,2-f][1,2,4]triazolo[4,3-a][1,4]diazepine;
1-benzyl-6-(4-chlorophenyl)-7,8,9,10-tetrahydro-4H-pyrido[4',3';4,5]thieno[3,2-f][1,2,4]triazolo[4,3-a][1,4]diazepine;
1-benzyl-6-phenyl-7,8,9,10-tetrahydro-4H-pyrido[4',3';4,5]thieno[3,2-f][1,2,4]triazolo[4,3-a][1,4]diazepine;
1-benzyl-6-(3-chlorophenyl)-7,8,9,10-tetrahydro-4H-pyrido[4',3';4,5]thieno[3,2-f][1,2,4]triazolo[4,3-a][1,4]diazepine;
1-methyl-6-(3-chlorophenyl)-7,8,9,10-tetrahydro-4H-pyrido[4',3';4,5]thieno[3,2-f][1,2,4]triazolo[4,3-a][1,4]diazepine;
1-butyl-6-(2-methylphenyl)-7,8,9,10-tetrahydro-4H-pyrido[4',3';4,5]thieno[3,2-f][1,2,4]triazolo[4,3-a][1,4]diazepine;
1-benzyl-6-(2-methylphenyl)-7,8,9,10-tetrahydro-4H-pyrido[4',3';4,5]thieno[3,2-f][1,2,4]triazolo[4,3-a][1,4]diazepine;
1-butyl-6-(2-methoxyphenyl)-7,8,9,10-tetrahydro-4H-pyrido[4',3';4,5]thieno[3,2-f][1,2,4]triazolo[4,3-a][1,4]diazepine;
1-heptyl-6-(2-chlorophenyl)-7,8,9,10-tetrahydro-4H-pyrido[4',3';4,5]thieno[3,2-f][1,2,4]triazolo[4,3-a][1,4]diazepine;
1-hexyl-6-(4-chlorophenyl)-7,8,9,10-tetrahydro-4H-pyrido[4',3';4,5]thieno[3,2-f][1,2,4]triazolo[4,3-a][1,4]diazepine;
1-pentyl-6-(4-chlorophenyl)-7,8,9,10-tetrahydro-4H-pyrido[4',3';4,5]thieno[3,2-f][1,2,4]triazolo[4,3-a][1,4]diazepine;
6-(2-chlorophenyl-7,8,9,10-tetrahydro-1-methyl-9-[2-(2-trifluoromethylphenyl)-1-oxoethyl]-4H-pyrido[4',3';4,5]thieno[3,2-f][1,2,4]triazolo[4,3-a][1,4]diazepine;
6-(2-chlorophenyl-7,8,9,10-tetrahydro-1-methyl-9-[2-(2-trifluoromethylphenyl)-1-thioxoethyl]-4H-pyrido[4',3';4,5]thieno[3,2-f][1,2,4]triazolo[4,3-a][1,4]diazepine;
6-(2-chlorophenyl-7,10-dihydro-1-methyl-N-(2-trifluoromethylphenyl)-4H-pyrido[4',3';4,5]thieno[3,2-f][1,2,4]triazolo[4,3-a][1,4]diazepine-9(8H)-carbothioamide;
6-(2-chlorophenyl-7,10-dihydro-1-methyl-N-(2-trifluoromethylphenyl)-4H-pyrido[4',3';4,5]thieno[3,2-f][1,2,4]triazolo[4,3-a][1,4]diazepine-9(8H)-carboxamide;
6-(2-chlorophenyl-7,10-dihydro-1-methyl-N-(2-trifluoromethylbenzyl)-4H-pyrido[4',3';4,5]thieno[3,2-f][1,2,4]triazolo[4,3-a][1,4]diazepine-9(8H)-carbothioamide;
6-(2-chlorophenyl-7,10-dihydro-1-methyl-N-benzyl-4H-pyrido[4',3';4,5]thieno[3,2-f][1,2,4]triazolo[4,3-a][1,4]diazepine-9(8H)-carboxamide;
phenyl ester of 6-(2-chlorophenyl)-7,10-dihydro-4H-pyrido[4',3';4,5]thieno[3,2-f][1,2,4]triazolo[4,3-a][1,4]diazepine-9(8H)-carboxylic acid;
6-(2-chlorophenyl)-7,10-dihydro-1,4-dimethyl-N-(2-trifluoromethylphenyl)-4H-pyrido[4',3';4,5]thieno[3,2-f][1,2,4]triazolo[4,3-a][1,4]diazepine-9(8H)-carbothioamide;
1-benzyl-6-(2-chlorophenyl)-7,10-dihydro-N-(2-trifluoromethylphenyl)-4H-pyrido[4',3';4,5]thieno[3,2-f][1,2,4]triazolo[4,3-a][1,4]diazepine-9(8H)-carbothioamide;

but also of the products of formula I as defined above and of which the substituents R,X,Y, $R_1$, $R_{2a}$, $R_{2b}$ and $R_3$ are respectively the following:

2-MeO-Ph; NH; S; 2-Cl; H; H; Me;
2-Me-Ph; NH; S; 2-Cl; H; H; Me;
2-isoPr-Ph; NH; S; 2-Cl; H; H; Me;
2-NC-Ph: NH; S; 2-Cl; H; H; Me;
2-$F_3$C-Ph; NH; S; 2-Cl; H; H; Et;
2-$F_3$C-Ph; NH; S; 2-Cl; H; H; H;
2-terBu-Ph; NH; S; 2-Cl; H; H; Me;
1-naphthyl; NH; S; 2-Cl; H; H; Me;
2-$F_3$CO-Ph; NH; S; 2-Cl; H; H; Me;
2-Cl-Ph; NH; S; 2-Cl; H; H; Me;
2-F-Ph; NH; S; 2-Cl; H; H; Me;
2-Et-Ph; NH; S; 2-Cl; H; H; Me;
2-PhO-Ph; NH; S; 2-Cl; H; H; Me;
2-Pr-Ph; NH; S; 2-Cl; H; H; Me;
2-Br-Ph; NH; S; 2-Cl; H; H; Me;
2-EtOC(O)-Ph; NH; S; 2-Cl; H; H; Me;
2-MeS-Ph; NH; S; 2-Cl; H; H; Me;
2-$NO_2$-Ph; NH; S; 2-Cl; H; H; Me;
2-MeO-5-Cl-Ph; NH; S; 2-Cl; H; H; Me;
2,4-(MeO)-Ph; NH; S; 2-Cl; H; H; Me;
2-Cl-5-$F_3$C-Ph; NH; S; 2-Cl; H; H; Me;
2-Me-5-Cl-Ph; NH; S; 2-Cl; H; H; Me;
2,3-Cl-Ph; NH; S; 2-Cl; H; H; Me;
2,5-Me-Ph; NH; S; 2-Cl; H; H; Me;
2,5-Cl-Ph; NH; S; 2-Cl; H; H; Me;
2-Me-5-F-Ph; NH; S; 2-Cl; H; H; Me;
2-$F_3$C-4-Br-Ph; NH; S; 2-Cl; H; H; Me;
2-$NO_2$-4-MeO-Ph; NH; S; 2-Cl; H; H; Me;
2-$NO_2$-4-Me-Ph; NH; S; 2-Cl; H; H; Me;
2-MeO-4-$NO_2$-Ph; NH; S; 2-Cl; H; H; Me;
2,5-Br-Ph; NH; S; 2-Cl; H; H; Me;
2-Cl-5-$NO_2$-Ph; NH; S; 2-Cl; H; H; Me;
2-$F_3$C-Ph; NH; S; 2-Cl; H; H; Pr;
2-$F_3$C-Ph; NH; S; 2-Cl; H; H; Bu;
2-$F_3$C-Ph; NH; S; H; H; H; Me;
2-$F_3$C-Ph; NH; S; 2-Cl; H; H; Ph;
2-$NO_2$-4-MeO-Ph; NH; S; 2-Cl; H; H; Pr;
2-$NO_2$-4-MeO-Ph; NH; S; 2-Cl; H; H; Bu;
2-Me$SO_2$-Ph; NH; S; 2-Cl; H; H; Me;
2-$F_3$C-4-Cl-Ph; NH; S; 2-Cl; H; H; Me;
2-$NO_2$-4-MeO-Ph; NH; S; 4-Cl; H; H; Bz;
2-$F_3$C-Ph; NH; S; 4-Cl; H; H; Me;
2-$NO_2$-4-MeO-Ph; NH; S; 2-Cl; H; H; pentyl;
2-$NO_2$-4-MeO-Ph; NH; S; 2-Cl; H; H; hexyl;
2-$NO_2$-4-MeO-Ph; NH; S; 3-Cl; H; H; Bz;
2-$NO_2$-4-F-Ph; NH; S; 2-Cl; H; H; Me;
2-$NO_2$-4-NC-Ph; NH; S; 2-Cl; H; H; Me;
2-$NO_2$-4-MeO-Ph; NH; S; 2-Cl; H; H; 1-naphthyl-methyl;
2-$NO_2$-4-MeO-Ph; NH; S; 2-Cl; H; H; 3-indolyl-methyl;
2-MeS-5-$F_3$C-Ph; NH; S; 2-Cl; H; H; Me;
2-$NO_2$-4-MeO-Ph; NH; S; 3-Cl; H; H; Me;
2-$NO_2$-4-MeO-Ph; NH; S; 2-Cl; H; H; Me;
2-$NO_2$-5-Cl-Ph; NH; S; 2-Cl; H; H; Me;
2-$NO_2$-5-Me-Ph; NH; S; 2-Cl; H; H; Me;
2-$NO_2$-4-EtO-Ph; NH; S; 2-Cl; H; H; Me;
2-$NO_2$-4-MeO-Ph; NH; S; 2-Cl; H; H; 4-MeO-Bz;
2-$NO_3$-4-Cl-Ph; NH; S; 2-Cl; H; H; Me;
2-Br-4-Me-Ph; NH; S; 2-Cl; H; H; Me;
2-$NO_2$-4-MeO-Ph; NH; S; 2-Cl; H; H; 4-HO-Bz;
2-$F_3$C-4-$NO_2$-Ph; NH; S; 2-Cl; H; H; Me;
2-$NO_2$-4-MeO-Ph; NH; S; H; H; H; Bz;
2-$NO_2$-4-MeO-Ph; NH; S; 2-Cl; H; H; Ph-$C_2H_4$;
2-$NO_2$-4-MeO-Ph; NH; S; 2-Cl; H; H; EtO$C_2H_4$;
3-$NO_2$-2-pyridinyl; NH; S; 2-Cl; H; H; Me;

2-F$_3$C-Ph; -; O; 2-Cl; H; H; Me;
Ph; -; S; 2-Cl; H; H; Me;
2-F$_3$C-Ph; CH$_2$; S; 2-Cl; H; H; Me;
2-NO$_2$-4-MeO-Ph; NH; S; 4-Cl; H; H; Me;
2-NO$_2$-Ph; CH$_2$; S; 2-Cl; H; H; Me;
2-NO$_2$-4-MeO-Ph; NH; S; 2-MeO; H; H; Bu;
2-NO$_2$-4-MeO-Ph; NH; S; 2-MeO; H; H; Bz;
2-NO$_2$-4-MeO-Ph; NH; 2-Me; H; Bu;
2-NO$_2$-4-MeO-Ph; NH; S; 2-Me; H; H; Bz;
2-NO$_2$-4-MeO-Ph; NH; S; 2-Cl; H; H; Ph-Ph;
2-NO$_2$-4-MeO-Ph; NH; S; 2-Cl; H; H; cyclohexylmethyl;
2-NO$_2$-4-MeO-Ph; NH; S; 2-Cl; H; H; (Me)$_2$NC$_2$H$_4$;
2-NO$_2$-4-MeO-Ph; NH; S; 2-Cl; H; H; 3-HO-Bz;
Ph; S; S; 2-Cl; H; H; Me;
2-NO$_2$-4-MeO-Ph; NH; S; 2-Cl; H; H; heptyl, as well as the salts of these compounds with mineral or organic acids when the molecule contains a basic group.

Among the compounds of formula I, some are new. A subject of the invention is therefore also a compound of general formula II

II in which
W' represents the hydrogen atom or a radical of formula R'—X'—C(Y')—;
R' represents the phenyl, naphthyl, indolyl or pyridyl radical, these radicals being optionally substituted by one or more identical or different substituents chosen from the following radicals: methyl, ethyl, propyl, isopropyl, butyl, ter-butyl, methoxy, ethoxy, methylthio, ethylthio, methoxycarbonyl, ethoxycarbonyl, methylsulphonyl, ethylsulphonyl, chloro, fluoro, bromo, trifluoromethyl, trifluoromethyloxy, hydroxy, nitro, cyano, phenyl, phenoxy or morpholino;
X' represents CH$_2$C$_2$H$_4$, CH$_2$NH, NH, O, S or a covalent bond;
Y' represents O or S;
R'$_1$ represents one or more identical or different groups, chosen from: the hydrogen atom, a chloro, methyl or methoxy radical;
R$_{2a'}$ and R$_{2b'}$ represent, independently, the hydrogen atom, a methyl radical;
R'$_3$ represents the hydrogen atom, methyl, ethyl, propyl, butyl, pentyl, hexyl, heptyl, methoxyethyl, ethoxyethyl, dimethylaminoethyl, cyclohexylmethyl, phenyl, diphenyl, benzyl optionally substituted by the hydroxy or methoxy radical, phenethyl, naphthylmethyl or indolylmethyl.

with the exclusion of the compounds of formula II in which
W' represents the hydrogen atom, R'$_1$ represents the chloro radical in ortho position; R$_{2a'}$ represents the hydrogen atom and R$_{2b'}$ represents the hydrogen atom or the methyl radical; R'$_3$ represents the methyl radical and
W' represents a radical of formula R'—X'—C(Y')— and
X'represents NH; Y' represents O; R'$_1$ represents the chloro radical in ortho position; R$_{2a'}$ and R$_{2b'}$ represents the hydrogen atom; R'$_3$ represents the methyl radical; R' represents the 4-terbutylphenyl, 4-trifluoromethylphenyl, 4-methoxyphenyl, 3,4,5-trimethoxyphenyl, 2,3-dichlorophenyl, 2,4-(difluoro)phenyl, 4-phenoxyphenyl; pyridyl; cyanophenyl radical;
X' represents NH; Y' represents S; R'$_1$ represents the chloro radical in ortho position; R$_{2a'}$ and R$_{2b'}$ represent the hydrogen atom; R'$_3$ represents the methyl radical; R' represents the 4-terbutylphenyl, 2,4-diterbutylphenyl, 2-trifluoromethylphenyl, 3-trifluoromethylphenyl, 4-trifluoromethylphenyl, 4-methoxyphenyl, 3,4,5-trimethoxyphenyl, 4-fluorophenyl, 4-(methylsulphonyl)phenyl radical;
X' represents CH$_2$NH; Y' represents O; R'$_1$ represents the chloro radical in ortho position; R$_{2a'}$ and R$_{2b'}$ represent the hydrogen atom; R'$_3$ represents the methyl radical; R' represents phenyl.
X' represents the oxygen atom or a covalent bond; Y' represents O; R$_1$ represents the chloro radical in ortho position; R$_{2a'}$ and R$_{2b'}$ represents the hydrogen atom; R'$_3$ represents the methyl radical; R' represents pyridyl or cyanophenyl;
X' represents CH$_2$; Y' represents O; R$_1$ represents the chloro radical in ortho position; R$_{2a'}$ and R$_{2b'}$ represents the hydrogen atom; R'$_3$ represents the methyl radical; R' represents phenyl or 4-fluorophenyl;
X' represents C$_2$H$_4$; Y' represents O; R$_1$ represents the chloro radical in ortho position; R$_{2a'}$ and R$_{2b'}$ represent the hydrogen atom; R'$_3$ represents the methyl radical; R' represents phenyl.

More particularly, a subject of the invention is a compound of general formula II in which W' represents a radical of formula R'—X'—C(Y')— and the substituents; R', X', Y', R'$_1$, R$_{2a'}$, R$_{2b'}$ and R'$_3$ represents respectively:
2-F$_3$C-Ph; CH$_2$; O; 2-Cl; H; H; Me;
2-F$_3$C-Ph; CH$_2$; S; 2-Cl; H; H; Me;
2-F$_3$C-Ph; NH; O; 2-Cl; H; H; Me;
2-F$_3$C-Ph; CH$_2$NH; S; 2-Cl; H; H; Me;
Ph; O; O; 2-Cl; H; H; Me;
2-F$_3$C-Ph; NH; S; 2-Cl; Me; H; Me;
2-F$_3$C-Ph; NH; S; 2-Cl; H; H; Bz;
3-F$_3$C-Ph; NH; O; 2-Cl; H; H; Me;
4-F$_3$C-Ph; NH; O; 2-Cl; H; H; Me;
2-iso-Pr-Ph; NH; S; 2-Cl; H; H; Me;
2-NC-Ph; NH; S; 2-Cl; H; H; Me;
2-F$_3$C-Ph; NH; S; 2-Cl; H; H; Et;
2-F$_3$C-Ph; NH; S; 2-Cl; H; H; H;
2-terBu-Ph; NH; S; 2-Cl; H; H; Me;
1-naphthyl; NH; S; 2-Cl; H; H; Me;
2-Ph-Ph; NH; S; 2-Cl; H; H; Me;
2-F$_3$CO-Ph; NH; S; 2-Cl; H; H; Me;
2-Cl-Ph; NH; S; 2-Cl; H; H; Me;
2-F-Ph; NH; S; 2-Cl; H; H; Me;
2-Et-Ph; NH; S; 2-Cl; H; H; Me;
2-PhO-Ph; NH; S; 2-Cl; H; H; Me;
2-Pr-Ph; NH; S; 2-Cl; H; H; Me;
2-EtO-Ph; NH; S; 2-Cl; H; H; Me;
Ph; NH; S; 2-Cl; H; H; Me;
2-Br-Ph; NH; S; 2-Cl; H; H; Me;
2-EtOC(O)-Ph; NH; S; 2-Cl; H; H; Me;
2-MeS-Ph; NH; S; 2-Cl; H; H; Me;

2-morpholino-Ph; NH; S; 2-Cl; H; H; Me;
2-NO$_2$-Ph; NH; S; 2-Cl; H; H; Me;
2,6-isoPr-Ph; NH; S; 2-Cl; H; H; Me;
2,6-Me-Ph; NH; S; 2-Cl; H; H; Me;
2,5-(MeO)-Ph; NH; O; 2-Cl; H; H; Me;
2-MeO-5-Cl-Ph; NH; S; 2-Cl; H; H; Me;
2,4-(MeO)-Ph; NH; S; 2-Cl; H; H; Me;
2-Cl-5-F$_3$C-Ph; NH; S; 2-Cl; H; H; Me;
2-Me-5-Cl-Ph; NH; S; 2-Cl; H; H; Me;
2,3-Cl-Ph; NH; S; 2-Cl; H; H; Me;
2,5-Me-Ph; NH; S; 2-Cl; H; H; Me;
2,5-Cl-Ph; NH; S; 2-Cl; H; H; Me;
2-Cl-4-Me-Ph; NH; S; 2-Cl; H; H; Me;
2-Me-3-Cl-Ph; NH; S; 2-Cl; H; H; Me;
2-Me-5-F-Ph; NH; S; 2-Cl; H; H; Me;
2,3-Me-Ph; NH; S; 2-Cl; H; H; Me;
2-F$_3$C-4-Br-Ph; NH; S; 2-Cl; H; H; Me;
2-NO$_2$-4-MeO-Ph; NH; S; 2-Cl; H; H; Me;
2-NO$_2$-4-Me-Ph; NH; S; 2-Cl; H; H; Me;
2-MeO-4-NO$_2$-Ph; NH; S; 2-Cl; H; H; Me;
2,5-Br-Ph; NH; S; 2-Cl; H; H; Me;
2-MeO-5-NO$_2$-Ph; NH; S; 2-Cl; H; H; Me;
2-Cl-4-NO$_2$-Ph; NH; S; 2-Cl; H; H; Me;
2-Cl-5-NO$_2$-Ph; NH; S; 2-Cl; H; H; Me;
2-F$_3$C-Ph; NH; S; 2-Cl; H; H; Pr;
2-F$_3$C-Ph; NH; S; 2-Cl; H; H; Bu;
3-Ph-6-MeO-Ph; NH; S; 2-Cl; H; H; Me;
2-F$_3$C-Ph; NH; S; H; H; H; Me;
2-F$_3$C-Ph; NH; S; 2-Cl; H; H; Ph;
2-NO$_2$-4-MeO-Ph; NH; S; 2-Cl; H; H; Pr;
2-NO$_2$-4-MeO-Ph; NH; S; 2-Cl; H; H; Bu;
2-NO$_2$-4-F$_3$C-Ph; NH; S; 2-Cl; H; H; Me;
2-MeSO$_2$-Ph; NH; S; 2-Cl; H; H; Me;
2-F$_3$C-4-Cl-Ph; NH; S; 2-Cl; H; H; Me;
2-NO$_2$-4-MeO-Ph; NH; S; 4-Cl; H; H; Bz;
2-F$_3$C-Ph; NH; S; 4-Cl; H; H; Me;
2-NO$_2$-4-MeO-Ph; NH; S; 2-Cl; H; H; pentyl;
2-NO$_2$-4-MeO-Ph; NH; S; 2-Cl; H; H; hexyl;
3,5-F$_3$C-Ph; NH; S; 2-Cl; H; H; Me;
2-NO$_2$-4-MeO-Ph; NH; S; 3-Cl; H; H; Bz;
2-NO$_2$-4-F-Ph; NH; S; 2-Cl; H; H; Me;
2-NO$_2$-4-NC-Ph; NH; S; 2-Cl; H; H; Me;
2-NO$_2$-4-MeO-Ph; NH; S; 2-Cl; H; H; 1-naphthyl-methyl;
2-NO$_2$-4-MeO-Ph; NH; S; 2-Cl; H; H; 3-indolyl-methyl;
2-MeS-5-F$_3$C-Ph; NH; S; 2-Cl; H; H; Me;
2-NO$_2$-4-MeO-Ph; NH; S; 3-Cl; H; H; Me;
2-NO$_2$-4-MeO-Ph; NH; S; 2-Cl; H; H; Me;
2-NO$_2$-4-HO-Ph; NH; S; 2-Cl; H; H; Me;
2-NO$_2$-5-Cl-Ph; NH; S; 2-Cl; H; H; Me;
2-NO$_2$-5-Me-Ph; NH; S; 2-Cl; H; H; Me;
2-NO$_2$-4-EtO-Ph; NH; S; 2-Cl; H; H; Me;
2-NO$_2$-4-MeO-Ph; NH; S; 2-Cl; H; H; 4-MeO-Bz;
2-NO$_2$-4-Cl-Ph; NH; S; 2-Cl; H; H; Me;
2-Br-4-Me-Ph; NH; S; 2-Cl; H; H; Me;
2-NO$_2$-4-MeO-Ph; NH; S; 2-Cl; H; H; 4-HO-Bz;
2-F$_3$C-4-NO$_2$-Ph; NH; S; 2-Cl; H; H; Me;
2-NO$_2$-4-MeO-Ph; NH; S; H; H; H; Bz;
2-NO$_2$-4-MeO-Ph; NH; S; 2-Cl; H; H; Ph-C$_2$H$_4$;
2-NO$_2$-4-MeO-Ph; NH; S; 2-Cl; H; H; EtOC$_2$H$_4$;
3-NO$_2$-2-pyridinyl; NH; S; 2-Cl; H; H; Me;
4-MeO-Ph; CH$_2$; O; 2-Cl; H; H; Me;
2-indolyl; O; 2-Cl; H; H; Me;
3-indolyl; CH$_2$; O; 2-Cl; H; H; Me;
4-HO-Ph; C$_2$H$_4$; O; 2-Cl; H; H; Me;
2-F$_3$C-Ph; -; O; 2-Cl; H; H; Me;
4-HO-Ph; O; 2-Cl; H; H; Me;
5-MeO-2-indolyl; -; O; 2-Cl; H; H; Me;
Ph; -; O; 2-Cl; H; H; Me;
Ph; -; S; 2-Cl; H; H; Me;
5-MeO-2-indolyl; -; S; 2-Cl; H; H; Me;
2-NO$_2$-Ph; CH$_2$; O; 2-Cl; H; H; Me;
2-F$_3$C-Ph; CH$_2$; S; 2-Cl; H; H; Me;
2-NO$_2$-4-MeO-Ph; NH; S; 4-Cl; H; H; Me;
2-NO$_2$-Ph; CH$_2$; S; 2-Cl; H; H; Me;
2-NO$_2$-4-MeO-Ph; NH; S; 2-MeO; H; H; Bu;
2-NO$_2$-4-MeO-Ph; NH; S; 2-MeO; H; H; Bz;
2-NO$_2$-4-MeO-Ph; NH; S; 2-Me; H; H; Bu;
2-NO$_2$-4-MeO-Ph; NH; S; 2-Me; H; H; Bz;
2-NO$_2$-4-MeO-Ph; NH; S; 2-Cl; H; H; Ph-Ph;
2-NO$_2$-4-MeO-Ph; NH; S; 2-Cl; H; H; cyclohexyl methyl;
2-NO$_2$-4-MeO-Ph; NH; S; 2-Cl; H; H; (Me)$_2$NC$_2$H$_4$;
2-NO$_2$-4-MeO-Ph; NH; S; 2-Cl; H; H; 3-HO-Bz;
2-pyridinyl; NH; S; 2-Cl; H; H; Me;
Ph; S; S; 2-Cl; H; H; Me;
Ph; O; S; 2-Cl; H; H; Me;
2-NO$_2$-4-MeO-Ph; NH; S; 2-Cl; H; H; heptyl, but also the compounds of formula II in which W' represents the hydrogen atom and the substituents R'$_1$, R$_{2a'}$, R$_{2b'}$ and R'$_3$ represent respectively:
2-Cl; H; H; butyl;
2-Cl; H; H; benzyl;
2-Cl; H; H; H;
2-Cl; H; H; ethyl;
2-Cl; H; H; propyl;
2-Cl; H; H; Ph;
2-Cl; H; H; pentyl;
2-Cl; H; H; hexyl;
2-Cl; H; H; 4-HO-Bz;
2-Cl; H; H; 4-MeO-Bz;
2-Cl; H; H; 1-naphthyl-methyl;
2-Cl; H; H; 3-indolyl-methyl;
2-Cl; H; H; Ph-C$_2$H$_4$;
2-Cl; H; H; Ph-Ph;
2-Cl; H; H; EtOC$_2$H$_4$;
2-Cl; H; H; cyclohexylmethyl;
2-Cl; H; H; 3-OH-Bz;
2-Cl; H; H; (Me)$_2$NC$_2$H$_4$;
H; H; H; Me;
4-Cl; H; H; Bz;
H; H; H; Bz;
4-Cl; H; H; Me;
3-Cl; H; H; benzyl;
3-Cl; H; H; Me;
2-Me; H; H; butyl;
2-Me; H; H; benzyl;
2-MeO; H; H; butyl;
2-Cl; H; H; heptyl;
2-Cl; H; H; hexyl;
2-Cl; H; H; butyl.

The compounds of formula I according to the invention and in which W represents the R—X—C(Y)— radical, can be prepared according to the process which consists of reacting a compound of formula (1)

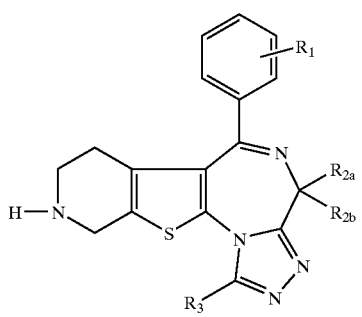
(1)

in which $R_1$, $R_{2a}$, $R_{2b}$ and $R_3$ have the meaning indicated above, with, according to the final product chosen A) either a compound of formula (2)

(2)

in which R, Y and n have the meaning indicated above, in order to form a compound of formula I in which X represents the —$(CH_2)_n$NH— radical;

B) or a compound of formula (3)

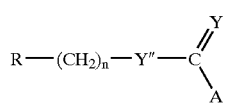
(3)

in which R, Y and n have the meaning indicated above, Y" represents O or S and A represents a halogen atom, in order to form a compound of formula I in which X represents the —$(CH_2)_n$—O— or —$(CH_2)_n$—S— radical;

C) or a compound of formula (4)

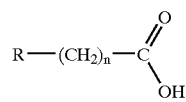
(4)

in which R and n have the meaning indicated above, in order to form a compound of formula I in which Y represents the —$(CH_2)_n$ radical and Y the oxygen atom, which compound can be optionally converted to a compound of formula I in which X represents the —$(CH_2)_n$ radical and Y the sulphur atom.

During the preparation according to route A), the addition of the compound of formula (2) as defined above, with a compound of formula (1) is easily carried out at a temperature close to 20° C. in a chlorinated solvent such as dichloromethane or 1,2-dichloroethane.

During the preparation according to route B), the conversion of compound (1) to a compound of formula I in which X represents the —$(CH_2)_n$Y"— radical, by reaction with a compound of formula (3), can be carried out at a temperature close to 20° C. in an inert solvent such as dichloromethane, and preferably in the presence of an acid acceptor such as triethylamine.

During the preparation according to route C), the compound of formula (1) is converted to a compound of formula I in which X represents the —$(CH_2)_n$ radical and Y the oxygen atom, by reaction with acid (4) under activation conditions similar to peptide coupling reactions. The reaction can be carried out at a temperature close to 20° C., in an inert solvent such as dimethylformamide, tetrahydrofuran or dichloromethane, and generally in the presence of an acid acceptor such as a tertiary amine such as for example, triethylamine or diisopropylethylamine. The amide thus obtained, can be converted to a compound of formula I in which X represents the —$(CH_2)_n$ radical and Y the sulphur atom, while heating the reaction medium at a temperature close to 90° C. in a polar solvent such as toluene or cyclohexanes, in the presence of a thiation agent such as Lawesson reagent.

The starting product of formula (1) corresponds to the product of formula I in which W represents a hydrogen atom. Such a compound can be obtained by reacting a compound of formula (5)

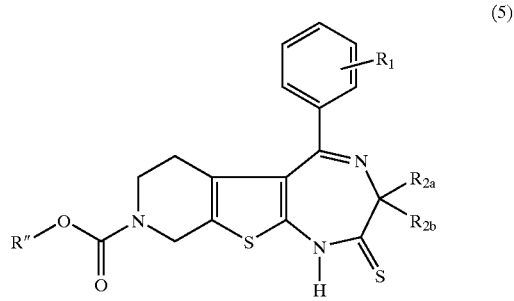
(5)

in which $R_1$, $R_{2a}$ and $R_{2b}$ have the meaning indicated above and R" represents a lower alkyl or lower arylalkyl radical, with a compound of formula (6)

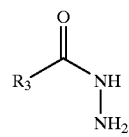
(6)

in which $R_3$ has the meaning indicated above, in order to obtain compound (7)

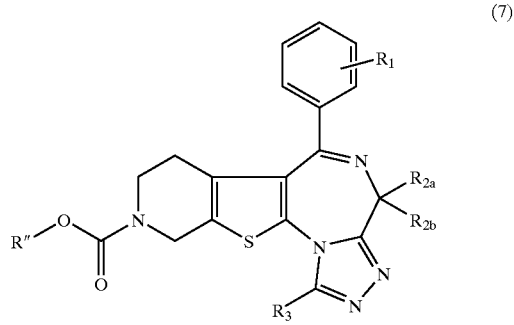
(7)

which compound is then subjected to a deprotection reaction of the carbamate in order to obtain product (1).

The compound of formula (1) can also be prepared by reacting a compound of formula (5) as defined above with hydrazine in order to obtain a compound of formula (8)

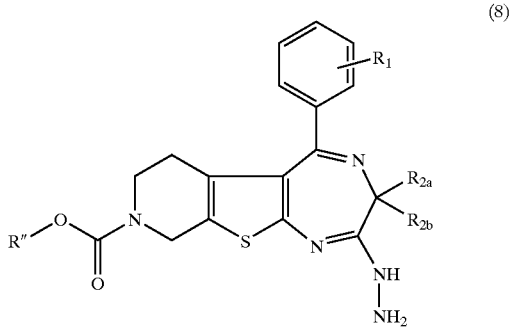

(8)

which compound is then reacted with a trialkyl orthoalkanoate type compound of formula (9)

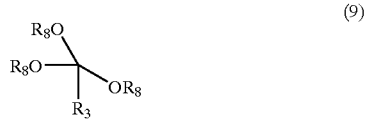

(9)

in which $R_8$ represents an alkyl group and $R_3$ has the meaning indicated above, in order to produce the compound of formula (7) as defined above which is then deprotected.

According to the first method for the preparation of compound 1, the compounds of formula (5) react on the compounds of formula (6) such as phenyl acethydrazide, 4-hydroxyphenyl acethydrazide, while heating an inert solvent such as toluene under reflux and in certain cases for reasons of solubility a mixture of polar solvents under reflux such as the 1,2-dichloroethane/methanol mixture. Preferably, compound (5) used is such that R" represents the ethyl or ter-butyl radical. The reaction is carried out in two stages with, in a first stage, formation of the corresponding azide followed by an intramolecular cyclization reaction leading to the compound of formula (7).

Deprotection of the carbamate can be carried out while heating in the presence of a mineral base such as sodium hydroxide in a lower aliphatic alcohol such as ethanol or by agitating at ambient temperature in highly acid medium such as for example hydrobromic acid (33% in acetic acid) in order to produce the compounds of formula (1). Other methods of cleaving the carbamate such as those described in Protective Groups in Organic Synthesis [T. W. Green, P. G. M. Wuts; 2nd Edition, J. Wiley and sons Inc., p. 364–6 (1991)] can also be used in so far as they are compatible with the substituents constituting the pyrido thieno triazolo diazepine skeleton of the compounds of general formula (7).

According to the second method, the compound of formula (5) reacts with hydrazine in solution in water while heating an aliphatic alcohol such as ethanol, isopropanol under reflux. This intermediate hydrazine compound is then reacted with a trialkyl orthoalkanoate compound of formula (9) in order to produce a compound of formula (7).

The product of formula (5) can be prepared according to the method described in patent FR2645153 or according to similar methods.

Certain products of formula (6) are commercially available; the others can be prepared by reacting under reflux of ethanol, the alkyl ester of $R_3$—$CO_2H$ acid on the hydrazine diluted to 35% in water. The reagents (9), (4) and (3) are in general marketed (for example by the firm Acros or Aldrich). The products of formula R—$(CH_2)_n$—N=C=Y are mostly commercially available or can be prepared by reacting the corresponding amine on (thio)phosgene according to methods known to a person skilled in the art.

In the case where $R_{2a}$ and $R_{2b}$ do not represents the hydrogen atom, the product of formula (1) can also be prepared in a similar fashion to that described in the Patent FR 2645153 with, for example, the use of 2-bromopropionyl bromide instead of bromoacetyl bromide in the second stage of the synthesis of the tetracycle.

Compounds I of the present invention have useful pharmacological properties. Thus it has been discovered that compounds I of the present invention have a high affinity for one (or more) of the somatostatin receptors. They can be used as non-peptide agonists or antagonists of somatostatin in a selective or non-selective manner.

The compounds of the present invention can therefore be used in different therapeutic applications. The compounds can advantageously be used to treat the pathological states or the diseases as presented above and in which one (or more) of the somatostatin receptors are involved.

An illustration of the pharmacological properties of the compounds of the invention will be found hereafter in the experimental part.

These properties make the products of formula I suitable for a pharmaceutical use. A subject of the present application is also, as medicaments, the products of formula II as defined above, as well as the addition salts with pharmaceutically acceptable mineral or organic acids of said products of formula II, as well as the pharmaceutical compositions containing, as active ingredient, at least one of the medicaments as defined above.

The invention therefore relates to the pharmaceutical compositions containing a compound of formula II according to the invention or a pharmaceutically acceptable addition salt of acid of this, in combination with a pharmaceutically acceptable support. The pharmaceutical composition can be in the form of a solid, for example, powders, granules, tablets, gelatin capsules or suppositories. Appropriate solid supports can be, for example, calcium phosphate, magnesium stearate, talc, sugars, lactose, dextran, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, similarly their mixtures, in varying proportions, in water, with added pharmaceutically acceptable oils or fats. The sterile liquid compositions can be used for intramuscular, intraperitoneal or subcutaneous injections and the sterile compositions can also be administered intravenously.

The following examples are presented to illustrate the above procedures and should in no event be considered as a limit to the scope of the invention.

EXPERIMENTAL PART

Example 1

1-butyl-6-(2-chlorophenyl)-7,8,9,10-tetrahydro-4H-pyrido[4',3';4,5]thieno[3,2-f][1,2,4]triazolo[4,3-a][1,4]diazepine 1st stage ethyl 5-(2-chlorophenyl)-2-hydrazino-6,9-dihydro-3H-pyrido[4',3';4,5]thieno[2,3-e][1,4]diazepine-8(7H)carboxylate Hydrazine at 35% in water (42 ml) is added at ambient temperature and under argon to a mixture containing 5-(2-chlorophenyl)-8-(ethoxycarbonyl)-6,7,8,9-tetrahydro-3H-pyrido[4',3';4,5]thieno[3,2-e][1,4]diazepine 2-thione (118.5 g, 0.282 mol) in 1740 ml of methanol. Agitation is maintained at this temperature for one hour. The precipitate is filtered on frit, washed with ethanol (100 ml) and with ether (2×200 ml) then dried under vacuum (61.9 g). The solvent contained in the filtrate is evaporated off. The solid is filtered then washed with methanol and with ether (44.1 g). The desired product is in the form of a yellow solid (total yield: 106 g, 90%). Melting point: 21.6° C.

NMR $^1$H (100 MHz, DMSO $d_6$, δ): 1.15 (t, 3H); 1.62 (m, 2H); 3.34 (m, 2H); 4.00 (q, 2H); 4.40–4.60 (m, 4H); 7.34–7.41 (m, 4H); 9.13 (m, 1H) IR (cm$^{-1}$): $\nu_{NH}$ (hydrazine): 2850–2950; $V_{C=O}$ (carbamate): 1690; 1600; 1310; 1370; 1240; 1120; 1050; 760.

2nd stage ethyl 1-butyl-6-(2-chlorophenyl)-7,10-dihydro-4H-pyrido[4',3';4,5]thieno[3,2-f][1,2,4]triazolo[4,3-a][1,4]diazepine-9(8H)-carboxylate A mixture containing ethyl 5-(2-chlorophenyl)-2-hydrazino-6,9-dihydro-3H-pyrido[4',3';4,5]thieno[2,3-e][1,4]-diazepine-8(7H) carboxylate (3 g, 7.2 mmol) and trimethyl orthovalerate (1.2 ml, 7.2 mol) in 15 ml of butanol is heated under reflux. Agitation is carried out for twelve hours at 20° C. until precipitation of the product. The latter is filtered on frit, washed with ethanol (15 ml), with isopropanol (15 ml), with isopropanol ether (15 ml) and with isopentene (15 ml) then dried under vacuum in order to obtain a white solid (2 g, 58%). Melting point: 190° C.

NMR $^1$H (400 MHz, DMSO d6, δ): 0.85 (t, 3H); 1.14 (m, 3H); 1.3 (m, 2H); 1.47 (m, 1H); 1.61 (m, 2H); 2.10 (d, 1H); 3.00 (t, 2H); 3.11 (m, 1H); 3.71 (m, 1H); 4.02 (q, 2H); 4.24 (d, 1H); 4.43 (m, 1H); 4.82 (d, 1H); 5.32 (d, 1H); 7.43–7.76 (m, 4H) IR (cm$^{-1}$); $\nu_{C=O}$ (carbamate): 1690; 1606; 1438; 1417; 1230; 1121; 761.

3rd stage 1-butyl-6-(2-chlorophenyl)-7,8,9,10-tetrahydro-4H-pyrido[4',3';4,5]thieno[3,2-f][1,2,4]triazolo[4,3-a][1,4]diazepine A mixture containing ethyl 1-butyl-6-(2-chlorophenyl)-7,10-dihydro-4H-pyrido[4',3';4,5]thieno[3,2-f][1,2,4]triazolo[4,3a][1,4]diazepine-9(8H)-carboxylate (1.98 g, 4.8 mmol) and potassium hydroxide (3 g, 0.052 mol) in 40 ml of ethanol is heated under reflux of ethanol and for 10 hours. The reaction medium is cooled down to 22° C. then filtered on frit. The frit is rinsed with 4 ml of ethanol. 80 ml of water is added to the filtrate. Five drops of acetic acid are added and the aqueous phase is extracted with dichloromethane (2×80 ml). The organic phase is dried over magnesium sulphate. The solvent is evaporated off with a rotary evaporator. The reaction mixture is agitated for one hour in a solvent mixture of isopropyl ether-isopentane-isopropanol (10-10-1 ml), followed by filtering on frit then washing with isopropyl ether and with isopentane. After drying under vacuum a white solid is obtained (0.9 g, 46%). Melting point: 224° C.

NMR $^1$H (400 MHz, DMSO d6, δ); 0.85 (t, 3H); 1.28–1.40 (m, 3H); 1.59 (m, 2H); 1.94 (m, 1H); 2.55 (m, 1H); 2.78 (m, 1H); 2.99 (t, 2H); 3.84 (q, 2H); 4.22 (d, 1H); 5.40 (d, 1H); 7.43–7.47 (m, (4H) IR (cm$^{-1}$): $\nu_{NH}$: 3268; 2930; 1600; 1430; 849; 747.

Example 2

1-benzyl-6-(2-chlorophenyl)-7,8,9,10-tetrahydro-4H-pyrido[4',3';4,5]thieno[3,2-f][1,2,4]triazolo[4,3-a][1,4]diazepine 1st stage Ethyl ester of 1-benzyl-6-(2-chlorophenyl)-7,10-dihydro-4H-pyrido[4',3';4,5]thieno[3,2-f][1,2,4]triazolo[4,3-a][1,4]diazepin-9(8H)-carboxylic acid A mixture containing 5-(2-chlorobenzoyl)-8-(ethoxycarbonyl)-6,7,8,9-tetrahydro-3H-pyrido[4',3';4,5]thieno[3,2-f][1,4]diazepine 2-thione (3 g, 0.007 mol) and the hydrazide of phenylacetic acid (1.18 g, 0.0077 mol) is heated under reflux in anhydrous toluene (40 ml) for 3 hours. After cooling down to ambient temperature, the precipitate is filtered on frit then agitated in a mixture of solvent (isopropyl ether/dichloromethane/isopentane: 90/8/2) for 12 hours. The solid is filtered on frit then washed with isopropyl ether, with isopropanol then with isopentane. After drying under vacuum for 12 hours, 2.8 g (76%) of a beige coloured solid is obtained. Melting point: 192° C.

NMR $^1$H (400 MHz CDCl$_3$, δ): 1.26 (t, 3H); 1.62–2.03 (m, 2H); 3.12 (m, 1H); 3.85 (m, 1H); 4.18 (m, 3H); 4.45 (s, 1H); 4.47 (q, 2H); 4.82 (m, 1H); 5.61 (d, 1H); 7.17–7.34 (m, 9H). IR (cm-1): 1694 $\nu$C=O(carbamate); 1434; 1420; 1232; 1126; 758; 727.

2nd stage 1-benzyl-6-(2-chlorophenyl)-7,8,9,10-tetrahydro-4H-pyrido[4',3';4,5]thieno[3,2-f][1,2,4]triazolo[4,3-a][1,4]diazepine A mixture containing ethyl ester of 1-benzyl-6-(2-chlorophenyl)-7,10-dihydro-4H-pyrido[4',3';4,5]thieno[3,2-f][1,2,4]triazolo[4,3-a][1,4]diazepine-9(8H)-carboxylic acid (3.6 g, 0.0071 mol) and potassium hydroxide (4.4 g, 0.078 mol) is heated under reflux in ethanol for 6 hours then left under agitation at ambient temperature for 48 hours. The solid is filtered on frit, washed with a minimum quantity of ethanol. After adding water, extraction is carried out with dichloromethane followed by drying over magnesium sulphate. The solvent is evaporated off and the product is purified by crystallization from an ethyl acetate/isopropanol 50/50 mixture, followed by leaving in a refrigerator for 48 hours then filtering on frit while washing with a solvent mixture: ethyl acetate-isopropanol (50-50). Washing is finally carried out with isopentene followed by drying under vacuum. 2.46 g (77%) of the desired product is obtained in the form of a beige coloured solid. Melting point: 191–192° C.

NMR $^1$H (400 MHz, CDCl$_3$, δ): 1.30 (m, 1H); 1.89 (m, 1H); 2.51 (m, 1H); 2.50 (se, 1H); 2.76 (m, 1H); 3.82 (q, 2H); 4.23 (dd, 1H); 4.44 (m, 2H); 5.33 (dd, 1H); 7.13–7.44 (m, 9H) IR (cm$^{-1}$): 3422, 2928, 1602, 1427, 1419, 1045, 1033, 759, 725, 695.

Example 3

1-methyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 1. Melting point: 202° C.

Example 4

6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point: 162° C.

Example 5

1-ethyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 1. Melting point: 242° C.

Example 6

1-propyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 1. Melting point >260° C.

Example 7

1-phenyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=262° C.

Example 8

1-pentyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=174° C.

Example 9

1-hexyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=194–198° C.

Example 10

1-(4-hydroxybenzyl)-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=220–230° C.

Example 11

1-(4-methoxybenzyl)-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=254–256° C.

Example 12

1-(1-naphthyl-methyl)-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=185–190° C.

Example 13

1-(3-indolyl-methyl)-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=196–200° C.

Example 14

1-phenethyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=216–218° C.

Example 15

1-diphenyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=210–214° C.

Example 16

1-ethoxyethyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=152° C.

Example 17

1-cyclohexylmethyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=188–190° C.

Example 18

1-(3-hydroxybenzyl)-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=242–246° C.

Example 19

1-(dimethylaminoethyl)-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=143–147° C.

Example 20

1-methyl-6-phenyl-7,8,9,10-tetrahydro-4H-pyrido[4',3';4,5]thieno[3,2-f][1,2,4]triazolo[4,3-a][1,4]diazepine It is obtained according to the method as described in Example 1. Melting point=240–244° C.

Example 21

1-benzyl-6-(4-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=238–242° C.

Example 22

1-benzyl-6-phenyl-7,8,9,10-tetrahydro-4H-pyrido[4',3';4,5]thieno[3,2-f][1,2,4]triazolo[4,3-a][1,4]diazepine It is obtained according to the method as described in Example 2. Melting point=214–218° C.

Example 23

1-methyl-6-(4-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 1. Melting point=262° C.

Example 24

1-benzyl-6-(3-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=170° C.

Example 25

1-methyl-6-(3-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 1. Melting point=160° C.

Example 26

1-butyl-6-(2-methylphenyl)-7,8,9,10-tetrahydro-4H-pyrido[4',3';4,5]thieno[3,2-f][1,2,4]triazolo[4,3-a][1,4]diazepine It is obtained according to the method as described in Example 1. Melting point=206° C.

Example 27

1-benzyl-6-(2-methylphenyl)-7,8,9,10-tetrahydro-4H-pyrido[4',3';4,5]thieno[3,2-f][1,2,4]triazolo[4,3-a][1,4]diazepine It is obtained according to the method as described in Example 2. Melting point=110–120° C.

Example 28

1-butyl-6-(2-methoxyphenyl)-7,8,9,10-tetrahydro-4H-pyrido[4',3';4,5]thieno[3,2-f][1,2,4]triazolo[4,3-a][1,4]diazepine It is obtained according to the method as described in Example 1. Melting point=190° C.

Example 29

1-heptyl-6-(2-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 1. Melting point=178–180° C.

Example 30

1-hexyl-6-(4-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 1. Melting point=190–192° C.

Example 31

1-pentyl-6-(4-chlorophenyl)-7,8,9,10-tetrahydro-4H-pyrido[4',3';4,5]thieno[3,2-f][1,2,4]triazolo[4,3-a][1,4]diazepine It is obtained according to the method as described in Example 1. Melting point=250° C.

Example 32

6-(2-chlorophenyl)-7,8,9,10-tetrahydro-1-methyl-9-[2-(2-trifluoromethylphenyl)-1-oxoethyl]-4H-pyrido[4',3';4,5]thieno[3,2-f][1,2,4]triazolo[4,3-a]diazepine A mixture containing 6-(2-chlorophenyl)-7,8,9,10-tetrahydro-1-methyl-4H-pyrido[4',3';4,5]thieno[3,2-f]1,2,4-triazolo[4,3-a]1,4-diazepine (2.22 g, 0.006 mol), 2-trifluoromethylphenyl acetic acid (1.35 g, 0.0066 mol), 1-(3-dimethylaminopropyl)-3-ethylcarbodiimide (1.26 g, 0.0066 mol) hydrochloride and triethylamine (1 ml, 0.0066 mol) in 40 ml of anhydrous dimethylformamide is agitated at a temperature close to 20° C. for 72 hours. The solvent is evaporated off with a rotary evaporator while entraining it with toluene. The crude reaction product is taken up in 30 ml of dichloromethane, washed with water and the organic phase is dried over magnesium sulphate and concentrated with a rotary evaporator. Then approximately 4 ml of dichloromethane is added to the reaction mixture then ether is added until precipitation. Agitation is carried out for a few minutes then filtering under vacuum while washing the precipitate with ether. The product obtained is dried under vacuum in order to obtain 2 g (61%) of expected compound in the form of a white solid. Melting point: 224–226° C.

HPLC-Conditions:
column: kromasyl C18 (150×4.6 mm)
Mobile phase: Solution A: 0.02% trifluoroacetic acid
Solution B: acetonitrile
Gradient:

| Temps (min.) | % A | % B | Curve |
|---|---|---|---|
| 0 | 90 | 10 | linear |
| 5 | 90 | 10 | |
| 14 | 30 | 70 | |
| 15 | 10 | 90 | |
| 25 | 10 | 90 | |
| 25.5 | 90 | 10 | |
| 55 | 90 | 10 | |

Retention time (min.): 14.82
Mass: MH$^+$ (exp.): 556.1; MH$^+$(theoretical): 556.12

Example 33

6-(2-chlorophenyl)-7,8,9,10-tetrahydro-1-methyl-9-[2-(2-trifluoromethylphenyl)-1-thioxoethyl]-4H-pyrido[4',3';4,5]thieno[3,2-f][1,2,4]triazolo[3,2-a][1,4]diazepine A mixture containing 6-(2-chlorophenyl)-7,8,9,10-tetrahydro-1-methyl-9-[2-(2-trifluoromethylphenyl)-1-oxoethyl]-4H-pyrido[4',3';4,5]thieno[3,2-f][1,2,4]triazolo[4,3-a][1,4]diazepine (1 g, 0.0018 mol) and Lawesson reagent (0.73 g, 0.0018 mol) is heated for 2 hours at a temperature close to 80° C. Agitation is maintained for 14 hours at a temperature close to 20° C. The precipitate is filtered on frit, washed with 30 ml of toluene and 30 ml of acetone, dried under vacuum. The expected product is isolated by flash chromatography on a silica column with a dichloromethane-methanol mixture (95-5) as eluent White solid. Melting point: >260° C.

HPLC-Conditions:
column: kromasyl C18 (150×4.6 mm)
Mobile phase: Solution A: 0.02% trifluoro acetic acid
Solution B: acetonitrile
Gradient:

| Temps (min.) | % A | % B | Curve |
|---|---|---|---|
| 0 | 90 | 10 | linear |
| 5 | 90 | 10 | |
| 25 | 10 | 90 | |
| 30 | 10 | 90 | |
| 31 | 90 | 10 | |
| 60 | 90 | 10 | |

Retention time (min.): 17.3.
Mass: MH$^+$ (exp.): 572.1; MH$^+$(theoretical): 572.09

Example 34

6-(2-chlorophenyl)-7,10-dihydro-1-methyl-N-(2-trifluoromethylphenyl)-4H-pyrido[4',3';4,5]thieno[3,2-f][1,2,4 triazolo[4,3-a][1,4]diazepine-9(8H)-carbothioamide 1st stage
2-trifluoromethylphenylisothiocyanate 2-trifluoromethylaniline (4.1 ml, 0.0325 mol) is added dropwise at a temperature close to 20° C. and under an argon atmosphere to a mixture containing thiophosgene (2.5 ml, 0.0326 mol) in 43 ml of water. Agitation is carried out for twelve hours then 30 ml of ethyl acetate is added. The organic phase is extracted with water then with a solution of 10% sodium bicarbonate and finally with a solution of salt water. The organic phase is dried over magnesium sulphate and the solvent is evaporated off with a rotary evaporator. The product obtained (6.85 g, 100%) is in the form of a brown oil which is used immediately for the following reaction.

2nd stage
6-(2-chlorophenyl)-7,10-dihydro-1-methyl-N-(2-trifluoromethylphenyl)-4H-pyrido[4',3';4,5]thieno[3,2-f][1,2,4]triazolo[4,3-a][1,4]diazepine-9(8H)-carbothioamide A mixture containing 2-trifluoromethylphenyl isothiocyanate (0.82 g, 0.004 mol) and 6-(2-chlorophenyl)-7,8,9,10-tetrahydro-1-methyl-4H-pyrido[4',3';4,5]thieno[3,2-f][1,2,4]triazolo[4,3-a][1,4]diazepine (1 g, 0.0027 mol) in 30 ml of 1,2-dichloroethane is agitated for 4 hours and at a temperature close to 20° C. Half the solvent is evaporated off with the rotary evaporator then 10 ml of ether is added. Agitation is carried out for 20 minutes at a temperature close to 20° C. followed by filtering on frit then washing with 20 ml of ether, with 20 ml of isopropyl ether and with 20 ml of isopentane. After drying under vacuum a cream coloured solid is obtained (1.21 g, 78%). Melting point: 190–192° C.

NMR $^1$H (400 MHz, DMSO d6, δ): 1.72 (m, 1H); 2.23 (m, 1H); 2.62 (s, 3H); 3.40 (m, 1H); 4.30 (m, 2H); 4.84 (d, 1H); 5.35 (d, 1H); 5.68 (d, 1H); 7.31–7.70 (m, 8H); 9.30 (s, 1H). IR: νNH(thiourea): 3250 cm$^{-1}$; 1607 cm$^{-1}$; 1525 cm$^{-1}$; 1381 cm$^{-1}$; 1317 cm$^{-1}$; 757 cm$^{-1}$

Example 35

6-(2-chlorophenyl)-7,10-dihydro-1-methyl-N-(2-trifluoromethylphenyl)-4H-pyrido[4',3';4,5]thieno[3,2-f][1,2,4]triazolo[4,3-a][1,4]diazepine-9(8H)-carboxamide A mixture containing 2-trifluoromethylphenyl isocyanate (1.5 g, 0.008 mol) and 6-(2-chlorophenyl)-7,8,9,10-tetrahydro-1-methyl-4H-pyrido[4',3';4,5]thieno[3,2-f][1,2,4]triazolo[4,3-a][1,4]diazepine (2.1 g, 0.0057 mol) in 50 ml of 1,2-dichloromethane is agitated at ambient temperature for 2 hours. The reaction mixture is evaporated to dryness. The residual oil is precipitated by adding diisopropyl acetate. After filtration on frit, washing is carried out with ether and the solid is dried at 65° C. overnight (2.2 g, 69%). A beige powder is obtained. Melting point: 196–198° C.

NMR $^1$H (400 MHz, DMSO d6, δ): 1.63 (m, 1H); 2.12 (m,1H); 2.61(s, 3H); 3.20 (m, 1H); 3.90 (m, 1H); 4.27 (d, 1H); 4.38 (d, 1H); 4.98 (d, 1H); 5.34 (d, 1H); 7.32–7.68 (m, 8H); 8.39 (s, 1H) IR: νNH(urea): 3333 cm$^{-1}$; νC=O (carbonyl urea): 1670 cm$^{-1}$; 1520 cm$^{-1}$; 1318 cm$^{-1}$; 1112 cm$^{-1}$; 764 cm$^{-1}$.

Example 36

6-(2-chlorophenyl)-7,10-dihydro-1-methyl-N-(2-trifluoromethylbenzyl)-4H-pyrido[4',3';4,5]thieno[3,2-f][1,2,4]triazolo[4,3-a][1,4]diazepine-9(8H)-carbothioamide 1st stage
2-trifluoromethylbenzylisothiocyanate A solution containing 2-trifluoromethylbenzylamine (3.50 g, 0.02 mol) in 50 ml of dichloromethane and a solution containing sodium bicarbonate (3.4 g, 0.04 mol) in 55 ml of water are added simultaneously over one hour at a temperature close to 20° C. to a solution of thiophosgene (2.28 g, 0.02 mol) in 15 ml of dichloromethane. Agitation is carried out for 30 minutes. The reaction mixture is decanted and the organic phase washed with 100 ml of water then with 100 ml of a solution of salt water. The organic phase is dried over magnesium sulphate and the solvent is evaporated off with a rotary evaporator. The expected compound is obtained in the form of an oil (3.50 g, 81%). Considering its reactivity, it is used immediately for the following reaction.

2nd stage
6-(2-chlorophenyl)-7,10-dihydro-1-methyl-N-(2-trifluoromethylbenzyl)-4H-pyrido[4',3';4,5]thieno[3,2-f][1,2,4]triazolo[4,3-a][1,4]diazepine-9(8H)-carbothioamide A mixture containing 2-trifluoromethylbenzylisothiocyanate (1 g, 0.0046 mol) and 6-(2-chlorophenyl)-7,8,9,10-tetrahydro-1-methyl-4H-pyrido[4',3';4,5]thieno[3,2-f][1,2,4]triazolo[4,3-a][1,4]diazepine (1.22 g, 0.0033 mol) in 20 ml of dichloromethane is agitated at a temperature close to 20° C. for 1 hour. The reaction mixture is evaporated to dryness. 40 ml of ethyl acetate is added to the residual oil. After separation of the insoluble part, the solvent is evaporated off. 40 ml of isopropyl ether is added until precipitation of the product then filtration on frit and washing with isopropyl ether. The solid obtained (1.2 g, 63%) is dried and a beige powder is obtained. Melting point: 178–184° C.

NMR $^1$H (400 MHz, DMSO d6, δ): 1.68 (m, 1H); 2.21 (m, 1H); 2.67 (s, 3H); 3.49 (m, 1H); 4.20 (m, 2H); 4.86 (m, 1H); 5.11 (m, 2H); 5.38 (m, 1H); 5.60 (m, 1H); 6.03 (t, 1H); 7.35–7.71 (m, 8H). IR: νNH(thiourea): 3266 cm$^{-1}$; 1607 cm$^{-1}$; 1313 cm$^{-1}$; 1117 cm$^{-1}$; 761 cm$^{-1}$

Example 37

6-(2-chlorophenyl)-7,10-dihydro-1-methyl-N-benzyl-4H-pyrido[4',3';4,5]thieno[3,2-f][1,2,4]triazolo[4,3-a][1,4]diazepine-9(8H)-carboxamide A mixture containing benzylisocyanate (133 g, 0.01 mol) and 6-(2-chlorophenyl)-7,8,9,10-tetrahydro-1-methyl-4H-pyrido[4',3';4,5]thieno][3,2-f][1,2,4]triazolo[3,2-a][1,4]diazepine (2.956 g, 0 0.008 mol) in 50 ml of benzene is agitated at ambient temperature for 2 hours and 30 minutes. The precipitate is filtered then washed with ether then crystallized from a solvent mixture: ethanol-isopropyl alcohol, followed by filtering warm then the reaction medium is left to crystallize cold overnight. After filtration of the crystals on frit, washing is carried out with isopropanol then with ether, followed by drying under vacuum for approximately forty hours at a temperature close to 75° C. (2.5 g, 62.5%). Melting point: 146–149° C.

NMR $^1$H (400 MHz, DMSO d6, δ): 1.77 (m, 1H); 2.11 (m,1H); 2.66 (s, 3H); 3.19 (m, 1H); 3.73 (m, 1H); 4.21 (d, 1H); 4.43 (t, 2H); 4.49 (d, 1H); 4.86 (d, 1H); 4.96 (t, 1H); 5.58 (d,1H); 7.27–7.35 (m, 9H). IR: νNH(urea): 3302 cm$^{-1}$; νC=O (carbonyl urea): 1653 cm$^{-1}$; 1550 cm$^{-1}$; 1268 cm$^{-1}$; 762 cm$^{-1}$; 724 cm$^{-1}$

Example 38 phenyl ester of 6-(2-chlorophenyl)-7,10-dihydro-4H-pyrido[4',3';4,5]thieno[3,2-f][1,2,4]triazolo[4,3-a][1,4]diazepine-9(8H)-carboxylic acid Phenylchloroformate (0.19 ml, 0.0015 mol) and triethylamine (0.2 ml, 0.0015 mol) are added dropwise at 0° C. and under an inert atmosphere to a mixture containing 6-(2-chlorophenyl)-7,10-dihydro-1-methyl-4H-pyrido[4',3';4,5]thieno[3,2-f][1,2,4]triazolo[4,3-a][1,4]diazepine (0.37 g, 0.001 mol) in 5 ml of dichloromethane. Agitation is carried out at ambient temperature for two hours. The organic phase is washed with water and dried over magnesium sulphate. The solvent is evaporated with a rotary evaporator, followed by taking up in ether until precipitation. Purification is carried out by flash chromatography on a silica column with dichloromethane-methanol: 95-5 as eluent and the column filtrate is concentrated with the rotary evaporator, followed by taking up in ether until a white precipitate (0.15 g, 31%) is obtained.

Melting point: 218–220° C.

HPLC-Conditions:

column: kromasyl C18 (150×4.6 mm)

Mobile phase: Solution A: 0.02% trifluoro acetic acid

Solution B: acetonitrile

Gradient:

| Temps (min.) | % A | % B | Curve |
| --- | --- | --- | --- |
| 5 | 90 | 10 | linear |
| 25 | 30 | 70 | |
| 30 | 30 | 70 | |
| 31 | 90 | 10 | |
| 45 | 90 | 10 | |

Retention time (min.): 14.82

Mass: MH⁺ (exp.): 490.07; MH⁺(theoretical): 490.11

Example 39

6-(2-chlorophenyl)-7,10-dihydro-1,4-dimethyl-N-(2-trifluoromethylphenyl)-4H-pyrido[4',3';4,5]thieno[3,2-f][1,2,4]triazolo[4,3-a][1,4]diazepine-9(8H)-carbothioamide A mixture containing 2-trifluoromethylphenylisothiocyanate (0.3 ml, 0.0015 mol) and 6-(2-chlorophenyl)-7,8,9,10 tetrahydro-1,4-dimethyl-4H-pyrido[4',3';4,5]thieno[3,2-f][1,2,4]triazolo[4,3-a][1,4]diazepine (0.383 mg, 0.001 mol) in 10 ml of anhydrous dichloromethane is agitated for two hours at a temperature close to 20° C. The reaction mixture is evaporated to dryness. Diisopropyl acetate is added until precipitation. After filtration of the insoluble part, evaporation to dryness is carried out. Ether is added until precipitation. The precipitate is filtered on frit and washed with ether then dried under vacuum (0.35 g, 59%) which produces a clear yellow powder. Melting point: 210–213° C.

NMR¹H (400 MHz, DMSO d6, δ): 1.73 (m, 1H); 1.89 (d,3H); 2.25 (d, 1H); 2.61 (s, 3H); 3.55 (m, 1H); 4.29–4.38 (m, 2H); 4.84 (d, 1H); 5.70 (d, 1H); 7.31–7.70 (m, 8H); 9.34 (s, 1H). IR: νNH (thiourea): 3408 cm⁻¹; 1525 cm⁻¹; 1319 cm⁻¹; 759 cm⁻¹

Example 40

1-benzyl-6-(2-chlorophenyl)-7,10-dihydro-N-(2-trifluoromethylphenyl)-4H-pyrido[4',3';4,5]thieno[3,2-f][1,2,4]triazolo[4,3-a][1,4]diazepine-9(8H)-carbothioamide Trifluoromethylphenylisothiocyanate (0.56 g, 0.0027 mol) is added to a mixture containing 1-benzyl-6-(2-chlorophenyl)-7,8,9,10-tetrahydro-4H-pyrido[4',3';4,5]thieno[3,2-f][1,2,4]triazolo[4,3-a][1,4]diazepine (0.8 g, 0.0018 mol) in anhydrous 1,2-dichloroethane (13 ml). The reaction medium is agitated at ambient temperature for 12 hours. The precipitate is filtered on frit then washed with isopropyl ether, with ethyl acetate then with isopentane and finally dried under vacuum. 0.28 g (24%) of final product is obtained in the form of a pale yellow coloured solid. Melting point: 239–240° C.

NMR¹H (400 MHz, CDCl₃, δ): 1.72 (m,1H); 2.15 (m,1H); 3.50 (m, 1H); 4.12 (m, 1H); 4.19 (d, 1H); 4.46 (q, 2H); 4.74 (d, 1H); 5.33 (d, 1H); 5.62 (d, 1H); 7.16–7.67 (m, 14H).

IR (cm⁻¹): 3349, 1527, 1318, 1128, 756. HPLC (UV): 95.8%

The products described in the table below which constitute Examples 41 to 148, are obtained according to the same processes as those described in Examples 32 to 40. The symbols used in the table are as follows: Me=methyl, Et=ethyl, Pr=propyl, Bu=butyl, Ph=phenyl, Bz=benzyl, Mp=melting point.

| Ex | R | X | Y | R₁ | R₂ₐ | R₂ᵦ | R₃ | Mp(° C.) |
|---|---|---|---|---|---|---|---|---|
| 41 | 2-MeO—Ph | NH | S | 2-Cl | H | H | Me | 165 |
| 42 | 2-Me—Ph | NH | S | 2-Cl | H | H | Me | 165 |
| 43 | 3-F₃C—Ph | NH | O | 2-Cl | H | H | Me | 222–223 |
| 44 | 4-F₃C—Ph | NH | O | 2-Cl | H | H | Me | 243–245 |
| 45 | 2-isoPr—Ph | NH | S | 2-Cl | H | H | Me | 212–213 |
| 46 | 2-NC—Ph | NH | S | 2-Cl | H | H | Me | 232–236 |
| 47 | 2-F₃C—Ph | NH | S | 2-Cl | H | H | Et | 225–230 |
| 48 | 2-F₃C—Ph | NH | S | 2-Cl | H | H | H | 250–255 |
| 49 | 2-terBu—Ph | NH | S | 2-Cl | H | H | Me | 180–182 |
| 50 | 1-naphthyl | NH | S | 2-Cl | H | H | Me | 194–196 |
| 51 | 2-Ph—Ph | NH | S | 2-Cl | H | H | Me | 165–170 |
| 52 | 2-F₃CO—Ph | NH | S | 2-Cl | H | H | Me | 220–223 |
| 53 | 2-Cl—Ph | NH | S | 2-Cl | H | H | Me | 200–203 |
| 54 | 2-F—Ph | NH | S | 2-Cl | H | H | Me | 206–208 |
| 55 | 2-Et—Ph | NH | S | 2-Cl | H | H | Me | 178–180 |
| 56 | 2-PhO—Ph | NH | S | 2-Cl | H | H | Me | 230–232 |
| 57 | 2-Pr—Ph | NH | S | 2-Cl | H | H | Me | 190–195 |
| 58 | 2-EtO—Ph | NH | S | 2-Cl | H | H | Me | 204–206 |
| 59 | Ph | NH | S | 2-Cl | H | H | Me | 206–210 |
| 60 | 2-Br—Ph | NH | S | 2-Cl | H | H | Me | 190–195 |
| 61 | 2-EtOC(O)—Ph | NH | S | 2-Cl | H | H | Me | 166–170 |
| 62 | 2-MeS—Ph | NH | S | 2-Cl | H | H | Me | 178–180 |
| 63 | 2-morpholino-Ph | NH | S | 2-Cl | H | H | Me | 242–246 |
| 64 | 2-NO₂—Ph | NH | S | 2-Cl | H | H | Me | 190–192 |
| 65 | 2,6-isoPr—Ph | NH | S | 2-Cl | H | H | Me | 160–165 |
| 66 | 2,6-Me—Ph | NH | S | 2-Cl | H | H | Me | 198–201 |
| 67 | 2,5-(MeO)—Ph | NH | O | 2-Cl | H | H | Me | 258–260 |
| 68 | 2-MeO-5-Cl—Ph | NH | S | 2-Cl | H | H | Me | 203–206 |
| 69 | 2,4-(MeO)—Ph | NH | S | 2-Cl | H | H | Me | 194–196 |
| 70 | 2-Cl-5-F₃C—Ph | NH | S | 2-Cl | H | H | Me | 218–220 |
| 71 | 2-Me-5-Cl—Ph | NH | S | 2-Cl | H | H | Me | 236–240 |
| 72 | 2,3-Cl—Ph | NH | S | 2-Cl | H | H | Me | 230–232 |
| 73 | 2,5-Me—Ph | NH | S | 2-Cl | H | H | Me | 192–196 |
| 74 | 2,5-Cl—Ph | NH | S | 2-Cl | H | H | Me | 234–236 |
| 75 | 2-Cl-4-Me—Ph | NH | S | 2-Cl | H | H | Me | 206–208 |
| 76 | 2-Me-3-Cl—Ph | NH | S | 2-Cl | H | H | Me | 248–252 |
| 77 | 2-Me-5-F—Ph | NH | S | 2-Cl | H | H | Me | 202–204 |
| 78 | 2,3-Me—Ph | NH | S | 2-Cl | H | H | Me | 225–228 |

-continued

| Ex | R | X | Y | $R_1$ | $R_{2a}$ | $R_{2b}$ | $R_3$ | Mp(° C.) |
|---|---|---|---|---|---|---|---|---|
| 79 | 2-$F_3$C-4Br—Ph | NH | S | 2-Cl | H | H | Me | 212–214 |
| 80 | 2-$NO_2$-4-MeO—Ph | NH | S | 2-Cl | H | H | Me | 248–250 |
| 81 | 2-$NO_2$-4-Me—Ph | NH | S | 2-Cl | H | H | Me | 262–264 |
| 82 | 2-MeO-4-$NO_2$—Ph | NH | S | 2-Cl | H | H | Me | 230–233 |
| 83 | 2,5-Br—Ph | NH | S | 2-Cl | H | H | Me | 260–264 |
| 84 | 2-MeO-5-$NO_2$—Ph | NH | S | 2-Cl | H | H | Me | 205–208 |
| 85 | 2-Cl-4-$NO_2$—Ph | NH | S | 2-Cl | H | H | Me | 244–248 |
| 86 | 2-Cl-5-$NO_2$—Ph | NH | S | 2-Cl | H | H | Me | 252–254 |
| 87 | 2-$F_3$C—Ph | NH | S | 2-Cl | H | H | Pr | 229–230 |
| 88 | 2-$F_3$C—Ph | NH | S | 2-Cl | H | H | Bu | 216 |
| 89 | 3-Ph-6-MeO—Ph | NH | S | 2-Cl | H | H | Me | 260–262 |
| 90 | 2-$F_3$C—Ph | NH | S | — | H | H | Me | 178–185 |
| 91 | 2-$F_3$C—Ph | NH | S | 2-Cl | H | H | Ph | 190–194 |
| 92 | 2-$NO_2$-4-MeO—Ph | NH | S | 2-Cl | H | H | Pr | 255–260 |
| 93 | 2-$NO_2$-4-MeO—Ph | NH | S | 2-Cl | H | H | Bu | 197–200 |
| 94 | 2-$NO_2$-4-$F_3$C—Ph | NH | S | 2-Cl | H | H | Me | 215–220 |
| 95 | 2-$MeSO_2$—Ph | NH | S | 2-Cl | H | H | Me | 190–195 |
| 96 | 2-$F_3$C-4-Cl—Ph | NH | S | 2-Cl | H | H | Me | 204–206 |
| 97 | 2-$NO_2$-4-MeO—Ph | NH | S | 4-Cl | H | H | Bz | 170–179 |
| 98 | 2-$F_3$C—Ph | NH | S | 4-Cl | H | H | Me | 192–196 |
| 99 | 2-$NO_2$-4-MeO—Ph | NH | S | 2-Cl | H | H | pentyl | 202–204 |
| 100 | 2-$NO_2$-4-MeO—Ph | NH | S | 2-Cl | H | H | hexyl | 103–105 |
| 101 | 3,5-$F_3$C—Ph | NH | S | 2-Cl | H | H | Me | >260 |
| 102 | 2-$NO_2$-4-MeO—Ph | NH | S | 3-Cl | H | H | Bz | 165–170 |
| 103 | 2-$NO_2$-4-F—Ph | NH | S | 2-Cl | H | H | Me | 176–180 |
| 104 | 2-$NO_2$-4-NC—Ph | NH | S | 2-Cl | H | H | Me | 206–210 |
| 105 | 2-$NO_2$-4-MeO—Ph | NH | S | 2-Cl | H | H | 1-napthyl-methyl | 215–218 |
| 106 | 2-$NO_2$-4-MeO—Ph | NH | S | 2-Cl | H | H | 3-indolyl-methyl | 231–235 |
| 107 | 2-MeS-5-$F_3$C—Ph | NH | S | 2-Cl | H | H | Me | 185–189 |
| 108 | 2-$NO_2$-4-MeO—Ph | NH | S | 3-Cl | H | H | Me | 192–196 |
| 109 | 2-$NO_2$-4-MeO—Ph | NH | S | 2-Cl | H | H | Me | 212–214 |
| 110 | 2-$NO_2$-4-HO—Ph | NH | S | 2-Cl | H | H | Me | 225–230 |
| 111 | 2-$NO_2$-5-Cl—Ph | NH | S | 2-Cl | H | H | Me | 196–200 |
| 112 | 2-$NO_2$-5-Me—Ph | NH | S | 2-Cl | H | H | Me | 202–204 |
| 113 | 2-$NO_2$-4-EtO—Ph | NH | S | 2-Cl | H | H | Me | 213–215 |
| 114 | 2-$NO_2$-4-MeO—Ph | NH | S | 2-Cl | H | H | 4-MeO—Bz | 178–180 |
| 115 | 2-$NO_2$-4-Cl—Ph | NH | S | 2-Cl | H | H | Me | 226–230 |
| 116 | 2-Br-4-Me—Ph | NH | S | 2-Cl | H | H | Me | 178–180 |
| 117 | 2-$NO_2$-4-MeO—Ph | NH | S | 2-Cl | H | H | 4-HO—Bz | 196–197 |
| 118 | 2-$F_3$C-4-$NO_2$—Ph | NH | S | 2-Cl | H | H | Me | 175–180 |
| 119 | 2-$NO_2$-4-MeO—Ph | NH | S | H | H | H | Bz | 201–202 |
| 120 | 2-$NO_2$-4-MeO—Ph | NH | S | 2-Cl | H | H | Ph—$C_2H_4$ | 165–170 |
| 121 | 2-$NO_2$-4-MeO—Ph | NH | S | 2-Cl | H | H | EtO$C_2H_4$ | 145–153 |
| 122 | 3-$NO_2$-pyridyl | NH | S | 2-Cl | H | H | Me | 224–226 |
| 123 | 4-MeO—Ph | $CH_2$ | O | 2-Cl | H | H | Me | 178–180 |
| 124 | 2-indolyl | — | O | 2-Cl | H | H | Me | >260 |
| 125 | 3-indolyl | $CH_2$ | O | 2-Cl | H | H | Me | 190–192 |
| 126 | 4-HO—Ph | $C_2H_4$ | O | 2-Cl | H | H | Me | 175–180 |
| 127 | 2-$F_3$C—Ph | — | O | 2-Cl | H | H | Me | 180–182 |
| 128 | 4-HO—Ph | $CH_2$ | O | 2-Cl | H | H | Me | 188–190 |
| 129 | 5-MeO-2-indolyl | — | O | 2-Cl | H | H | Me | >250 |
| 130 | Ph | — | O | 2-Cl | H | H | Me | 246–248 |
| 131 | Ph | — | S | 2-Cl | H | H | Me | 200–202 |
| 132 | 5-MeO-2-indolyl | — | S | 2-Cl | H | H | Me | >260 |
| 133 | 2-$NO_2$—Ph | $CH_2$ | O | 2-Cl | H | H | Me | 204–206 |
| 134 | 2-$F_3$C—Ph | $CH_2$ | S | 2-Cl | H | H | Me | >260 |
| 135 | 2-$NO_2$-4-MeO—Ph | NH | S | 4-Cl | H | H | Me | 185–190 |
| 136 | 2-$NO_2$—Ph | $CH_2$ | S | 2-Cl | H | H | Me | 180–185 |
| 137 | 2-$NO_2$-4-MeO—Ph | NH | S | 2-MeO | H | H | Bu | 220–224 |
| 138 | 2-$NO_2$-4-MeO—Ph | NH | S | 2-MeO | H | H | Bz | 150–154 |
| 139 | 2-$NO_2$-4-MeO—Ph | NH | S | 2-Me | H | H | Bu | 191–193 |
| 140 | 2-$NO_2$-4-MeO—Ph | NH | S | 2-Me | H | H | Bz | 175 |
| 141 | 2-$NO_2$-4-MeO—Ph | NH | S | 2-Cl | H | H | Ph—Ph | 237–240 |
| 142 | 2-$NO_2$-4-MeO—Ph | NH | S | 2-Cl | H | H | cyclohexyl methyl | 204–206 |
| 143 | 2-$NO_2$-4-MeO—Ph | NH | S | 2-Cl | H | H | $(Me)_2$N—$C_2H_4$ | 179–182 |
| 144 | 2-$NO_2$-4-MeO—Ph | NH | S | 2-Cl | H | H | 3-HO—Bz | 212–217 |
| 145 | 2-pyridyl | NH | S | 2-Cl | H | H | Me | 216–218 |
| 146 | Ph | S | S | 2-Cl | H | H | Me | 264–266 |
| 147 | Ph | O | O | 2-Cl | H | H | Me | 178–180 |
| 148 | 2-$NO_2$-4-MeO—Ph | NH | S | 2-Cl | H | H | heptyl | 198–200 |

Pharmacological Study

Study of the bond to somatostatin receptors

The affinity of the compounds of the invention on human somatostatin receptors is determined by measurement of the inhibition of the bond of somatostatin-14 labeled with iodine-125 ([125I-Tyr11]SRIF-14) on the receptors of transfected CHO-K11 cells.

The human genes coding for each of the sub-types of somatostatin receptors, sst1, sst2, sst3, sst4 and sst5, have been isolated and sub-cloned (*Proc. Natl. Acad. Sci. USA* 1992, 89, 251–255; *J. Biol. Chem.* 1992, 267, 20422–20428; *Mol. Pharmacol.* 1992, 42, 2136–2142; *Proc. Natl. Acad. Sci. USA* 1993, 90, 4196–4200; *Mol. Pharmacol.* 1994, 46, 291–298). The expression vectors were constructed and the cloned cell lines were obtained by transfection in mammalian CHO-K1 cells. The plasmid pRSV-neo was included as a selection factor.

The CHO-K1 cells which express in a stable fashion the human somatostatin receptors are cultured in an RPMI 1640 medium containing 10% of foetal calf serum and 0.4 mg/ml of geneticin. The cells are collected with EDTA at 0.5 mM and centrifuged at 500 g for 5 minutes at 4° C. The pellet is resuspended in Tris 50 mM, pH 7.4 and centrifuged twice at 500 g for 5 minutes at 4° C. The cells are lysed by sonication then centrifuged at 39000 g for 10 minutes at 4° C. The pellet is resuspended in the same buffer and centrifuged at 50000 g for 5 minutes at 4° C. The cell membranes obtained are stored at −80° C. until the day of the experiments.

The competitive inhibition experiments of the bond of [125I-Tyr11]SRIF-14 are carried out in duplicate in 96-well plates. The cell membranes at 10 (sst2 and ss5) or 20 (sst1, sst 3 and sst4) μg of proteins/well, were incubated with [125I-Tyr11]SRIF-14 at 0.05 nM (sst2) or 0.1 nM (sst1, sst3, sst4 or sst5) for 500 (sst3), 60 (sst1 and sst2), 70 (sst5) or 90 (sst4) minutes at 37° C. in a HEPES 50 mM, pH 7.4, BSA 0.2%, MgCl$_2$ 5 mM, Trasylol 200 KIU/ml, bacitricin 0.02 mg/ml, phenylmethylsulphonyl fluoride 0.02 mg/ml buffer.

After the incubation period, [125I-Tyr11]SRIF-14 free or bound to the somatostatin receptors is separated on a filtration unit (Filtermate 196, Packard) with Unifilter GF/C (Packard) filter plates pretreated with 0.1% polyethylenimine. After washing with HEPES 50 mM, the radioactivity present on the filters is measured using a Top Count (Packard) counter.

The specific bond is obtained by subtracting the non-specific bond (determined in the presence of 0.1 μM of somatostatin-14) from the total bond. The results are analyzed by non-linear regression (MDL) and the inhibition constants (Ki) determined are comprised between 10 and 10000 nM.

What is claimed is:

1. A method for treating a condition selected from the group consisting of acromegalia, hypophyseal adenomas and endocrinic gastroenteropancreatic tumors in warm-blooded animals comprising administering to warm-blooded animals in need thereof an effective amount of a compound selected from the group consisting of a compound of the formula

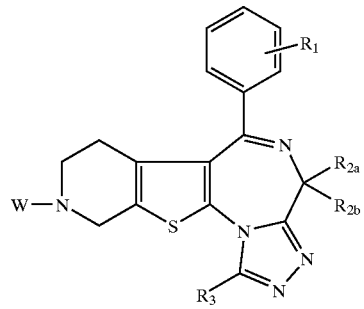

wherein W is hydrogen or R—X—C(Y)—, R is unsubstituted or substituted aryl or heteroaryl with at least one substituent selected from the group consisting of lower alkyl, lower alkoxy, lower alkylthio, lower alkoxycarbonyl, lower alkylsulfonyl, halogen, —CF$_3$, —OCF$_3$, —OH, —NO$_2$, —CN, aryl, aryloxy, cycloalkyl and heterocycloalkyl, X is —(CH$_2$)$_n$—Z, Z is selected from the group consisting of a covalent bond, —NH—, —O— and —S—, n is 0, 1 or 2, Y is oxygen or sulfur, R$_1$ is selected from the group consisting of hydrogen, —OH, halogen, lower alkyl and lower alkoxy, the alkyl and alkoxy being unsubstituted or substituted with at least one member of the group consisting of —CF$_3$, lower alkoxy, —NH$_2$ and mono- and di-lower alkylamino, R$_{2a}$ and R$_{2b}$ are individually hydrogen or methyl, R$_3$ is selected from the group consisting of hydrogen, halogen, —NO$_2$, —CN, unsubstituted or substituted alkyl of 1 to 10 carbon atoms, unsubstituted or substituted lower alkenyl, unsubstituted or substituted alkynyl, unsubstituted or substituted cycloalkyl, unsubstituted or substituted cycloalkylalkyl, unsubstituted or substituted aryl, unsubstituted or substituted aralkyl, unsubstituted or substituted lower aryloxyalkyl, unsubstituted or substituted heteroaryl, unsubstituted or substituted heteroarylalkyl and —Z$_{31}$R$_{31}$, the substituents being selected from the group consisting of halogen, aryl,

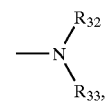

and —Z$_{32}$—R$_{34}$, Z$_{31}$ is selected from the group consisting of —O—, —C(O)—, —OC(O)— and —S—, R$_{31}$ is selected from the group consisting of hydrogen, lower alkyl, aryl and lower aralkyl, R$_{32}$ and R$_{33}$ are individually selected from the group consisting of hydrogen, lower alkyl, aralkyl and alkylcarbonyl or together with the nitrogen form a heterocycloalkyl, Z$_{32}$ is selected from the group consisting of oxygen, sulfur, —C(O)—, —S(O)—, —O—CO— and —SO$_2$—, R$_{34}$ is selected from the group consisting of hydrogen, lower alkyl, aryl and lower aralkyl and its non-toxic pharmaceutically acceptable salts sufficient to treat said condition.

2. The method of claim 1 wherein

W is hydrogen or R—X—C(Y)—;

R is aryl or heteroaryl, both unsubstituted or substituted by at least one member selected from the group consisting of lower alkyl, lower alkoxy, lower alkylthio, lower alkoxycarbonyl, lower alkylsulfonyl, halo, trifluoromethyl, trifluoromethoxy, hydroxy, nitro, cyano, aryl, aryloxy or heterocycloalkyl;

$R_1$ is at least one member of the group consisting of hydrogen, halo, lower alkyl and lower alkoxy;

$R_{2a}$ and $R_{2b}$ are independently, hydrogen or methyl;

$R_3$ is selected from the group consisting of hydrogen, alkyl of 1 to 10 carbon atoms, cycloalkylalkyl, aryl, lower arylalkyl or heteroarylalkyl the alkyl, cycloalkyl, aryl and heteroaryl are unsubstituted or substituted by at least one member of the group consisting of aryl; —$NR_{32}R_{33}$ in which either $R_{32}$ and $R_{33}$ are independently, hydrogen or lower alkyl and —$Z_{32}R_{34}$ in which $Z_{32}$ is O and $R_{34}$ is hydrogen or lower alkyl.

3. The method of claim 1 wherein

W is selected from the group consisting of hydrogen or R—X—C(Y)—; R is selected from the group consisting of phenyl, naphthyl, indolyl and pyridyl, all unsubstituted or substituted by at least one member selected from the group consisting of methyl, ethyl, propyl, isopropyl, butyl, tert-butyl, methoxy, ethoxy, methylthio, ethylthio, methoxycarbonyl, ethoxycarbonyl, methylsulfonyl, ethylsulfonyl, chloro, fluoro, bromo, trifluoromethyl, trifluoromethoxy, hydroxy, nitro, cyano, phenyl, phenoxy and morpholino;

X is —NH—,

Y is selected from the group consisting of O or S;

$R_1$ is selected from the group consisting of one of a hydrogen atom, a chloro, methyl or methoxy radical;

$R_{2a}$ and $R_{2b}$ are selected from the group consisting of a hydrogen atom or a methyl;

$R_3$ is selected from the group consisting of a hydrogen atom, methyl, ethyl, propyl, butyl, pentyl, hexyl, heptyl, methoxyethyl, ethoxyethyl, dimethylmainoethyl, cyclohexylmethyl, phenyl, diphenyl, benzyl unsubstituted or substituted by the hydroxy or methoxy, phenethyl, naphthylmethyl or indolylmethyl.

4. The method of claim 1 wherein the compound is selected from the group consisting of:

1-butyl-6-(2-chlorophenyl)-7,8,9,10-tetrahydro-4H-pyrido[4',3';4,5]thieno[3,2-f][1,2,4]triazolo[4,3-a][1,4]diazepine;

1-benzyl-6-(2-chlorophenyl)-7,8,9,10-tetrahydro-4H-pyrido[4',3';4,5]thieno[3,2-f][1,2,4]triazolo[4,3-a][1,4]diazepine;

1-methyl-6-(2-chlorophenyl)-7,8,9,10-tetrahydro-4H-pyrido[4',3';4,5]thieno[3,2-f][1,2,4]triazolo[4,3-a][1,4]diazepine;

6-(2-chlorophenyl)-7,8,9,10-tetrahydro-4H-pyrido[4',3';4,5]thieno[3,2-f][1,2,4]triazolo[4,3-a][1,4]diazepine;

1-ethyl-6-(2-chlorophenyl)-7,8,9,10-tetrahydro-4H-pyrido[4',3';4,5]thieno[3,2-f][1,2,4]triazolo[4,3-a][1,4]diazepine;

1-propyl-6-(2-chlorophenyl)-7,8,9,10-tetrahydro-4H-pyrido[4',3';4,5]thieno[3,2-f][1,2,4]triazolo[4,3-a][1,4]diazepine;

1-phenyl-6-(2-chlorophenyl)-7,8,9,10-tetrahydro-4H-pyrido[4',3';4,5]thieno[3,2-f][1,2,4]triazolo[4,3-a][1,4]diazepine;

1-pentyl-6-(2-chlorophenyl)-7,8,9,10-tetrahydro-4H-pyrido[4',3';4,5]thieno[3,2-f][1,2,4]triazolo[4,3-a][1,4]diazepine;

1-hexyl-6-(2-chlorophenyl)-7,8,9,10-tetrahydro-4H-pyrido[4',3';4,5]thieno[3,2-f][1,2,4]triazolo[4,3-a][1,4]diazepine;

1-(4-hydroxybenzyl)-6-(2-chlorophenyl)-7,8,9,10-tetrahydro-4H-pyrido[4',3';4,5]thieno[3,2-f][1,2,4]triazolo[4,3-a][1,4]diazepine;

1-(4-methoxybenzyl)-6-(2-chlorophenyl)-7,8,9,10-tetrahydro-4H-pyrido[4',3';4,5]thieno[3,2-f][1,2,4]triazolo[4,3-a][1,4]diazepine;

1-(1-naphthyl-methyl)-6-(2-chlorophenyl)-7,8,9,10-tetrahydro-4H-pyrido[4',3';4,5]thieno[3,2-f][1,2,4]triazolo[4,3-a][1,4]diazepine;

1-(3-indolyl-methyl)-6-(2-chlorophenyl)-7,8,9,10-tetrahydro-4H-pyrido[4',3';4,5]thieno[3,2-f][1,2,4]triazolo[4,3-a][1,4]diazepine;

1-phenethyl-6-(2-chlorophenyl)-7,8,9,10-tetrahydro-4H-pyrido[4',3';4,5]thieno[3,2-f][1,2,4]triazolo[4,3-a][1,4]diazepine;

1-diphenyl-6-(2-chlorophenyl)-7,8,9,10-tetrahydro-4H-pyrido[4',3';4,5]thieno[3,2-f][1,2,4]triazolo[4,3-a][1,4]diazepine;

1-ethoxyethyl-6-(2-chlorophenyl)-7,8,9,10-tetrahydro-4H-pyrido[4',3';4,5]thieno[3,2-f][1,2,4]triazolo[4,3-a][1,4]diazepine;

1-cyclohexylmethyl-6-(2-chlorophenyl)-7,8,9,10-tetrahydro-4H-pyrido[4',3';4,5]thieno[3,2-f][1,2,4]triazolo[4,3-a][1,4]diazepine;

1-(3-hydroxybenzyl)-6-(2-chlorophenyl)-7,8,9,10-tetrahydro-4H-pyrido[4',3';4,5]thieno[3,2-f][1,2,4]triazolo[4,3-a][1,4]diazepine;

1-(dimethylaminoethyl)-6-(2-chlorophenyl)-7,8,9,10-tetrahydro-4H-pyrido[4',3';4,5]thieno[3,2-f][1,2,4]triazolo[4,3-a][1,4]diazepine;

1-methyl-6-phenyl-7,8,9,10-tetrahydro-4H-pyrido[4',3';4,5]thieno[3,2-f][1,2,4]triazolo[4,3-a][1,4]diazepine;

1-benzyl-6-(4-chlorophenyl)-7,8,9,10-tetrahydro-4H-pyrido[4',3';4,5]thieno[3,2-f][1,2,4]triazolo[4,3-a][1,4]diazepine;

1-benzyl-6-phenyl-7,8,9,10-tetrahydro-4H-pyrido[4',3';4,5]thieno[3,2-f][1,2,4]triazolo[4,3-a][1,4]diazepine;

1-methyl-6-(4-chlorophenyl)-7,8,9,10-tetrahydro-4H-pyrido[4',3';4,5]thieno[3,2-f][1,2,4]triazolo[4,3-a][1,4]diazepine;

1-benzyl-6-(3-chlorophenyl)-7,8,9,10-tetrahydro-4H-pyrido[4',3';4,5]thieno[3,2-f][1,2,4]triazolo[4,3-a][1,4]diazepine;

1-methyl-6-(3-chlorophenyl)-7,8,9,10-tetrahydro-4H-pyrido[4',3';4,5]thieno[3,2-f][1,2,4]triazolo[4,3-a][1,4]diazepine;

1-butyl-6-(2-methylphenyl)-7,8,9,10-tetrahydro-4H-pyrido[4',3';4,5]thieno[3,2-f][1,2,4]triazolo[4,3-a][1,4]diazepine;

1-benzyl-6-(2-methylphenyl)-7,8,9,10-tetrahydro-4H-pyrido[4',3';4,5]thieno[3,2-f][1,2,4]triazolo[4,3-a][1,4]diazepine;

1-butyl-6-(2-methoxyphenyl)-7,8,9,10-tetrahydro-4H-pyrido[4',3';4,5]thieno[3,2-f][1,2,4]triazolo[4,3-a][1,4]diazepine;

1-heptyl-6-(2-chlorophenyl)-7,8,9,10-tetrahydro-4H-pyrido[4',3';4,5]thieno[3,2-f][1,2,4]triazolo[4,3-a][1,4]diazepine;

1-hexyl-6-(4-chlorophenyl)-7,8,9,10-tetrahydro-4H-pyrido[4',3';4,5]thieno[3,2-f][1,2,4]triazolo[4,3-a][1,4]diazepine;

1-pentyl-6-(4-chlorophenyl)-7,8,9,10-tetrahydro-4H-pyrido[4',3';4,5]thieno[3,2-f][1,2,4]triazolo[4,3-a][1,4]diazepine;

6-(2-chlorophenyl-7,8,9,10-tetrahydro-1-methyl-9-[2-(2-trifluoromethylphenyl)-1-oxoethyl]-4H-pyrido[4',3';4,5]thieno[3,2-f][1,2,4]triazolo[4,3-a][1,4]diazepine;

6-(2-chlorophenyl-7,10-dihydro-1-methyl-N-(2-trifluoromethylphenyl)-4H-pyrido[4',3';4,5]thieno[3,2-f][1,2,4]triazolo[4,3-a][1,4]diazepine-9(8H)-carbothioamide;

6-(2-chlorophenyl-7,10-dihydro-1-methyl-N-(2-trifluoromethylphenyl)-4H-pyrido[4',3';4,5]thieno[3,2-f][1,2,4]triazolo[4,3-a][1,4]diazepine-9(8H)-carboxamide;

6-(2-chlorophenyl-7,10-dihydro-1-methyl-N-(2-trifluoromethylbenzyl)-4H-pyrido[4',3';4,5]thieno[3,2-f][1,2,4]triazolo[4,3-a][1,4]diazepine-9(8H)-carbothioamide;

6-(2-chlorophenyl-7,10-dihydro-1-methyl-N-benzyl-4H-pyrido[4',3';4,5]thieno[3,2-f][1,2,4]triazolo[4,3-a][1,4]diazepine-9(8H)-carboxamide;

phenyl ester of 6-(2-chlorophenyl)-7,10-dihydro-4H-pyrido[4',3';4,5]thieno[3,2-f][1,2,4]triazolo[4,3-a][1,4]diazepine-9(8H)-carboxylic acid;

6-(2-chlorophenyl)-7,10-dihydro-1,4-dimethyl-N-(2-trifluoromethylphenyl)-4H-pyrido[4',3';4,5]thieno[3,2-f][1,2,4]triazolo[4,3-a][1,4]diazepine-9(8H)-carbothioamide;

1-benzyl-6-(2-chlorophenyl)-7,10-dihydro-N-(2-trifluoromethylphenyl)-4H-pyrido[4',3';4,5]thieno[3,2-f][1,2,4]triazolo[4,3-a][1,4]diazepine-9(8H)-carbothioamide;

or its substituents R, X, Y, $R_1$, $R_{2a}$, $R_{2b}$ and $R_3$ are respectively the following:

2-MeO-Ph; NH; S; 2-Cl; H; H; Me;
2-Me-Ph; NH; S; 2-Cl; H; H; Me;
2-isoPr-Ph; NH; S; 2-Cl; H; H; Me;
2-NC-Ph; NH; S; 2-Cl; H; H; Me;
2-$F_3$C-Ph; NH; S; 2-Cl; H; H; Et;
2-$F_3$C-Ph; NH; S; 2-Cl; H; H; H;
2-terBu-Ph; NH; S; 2-Cl; H; H; Me;
1-naphthyl; NH; S; 2-Cl; H; H; Me;
2-$F_3$CO-Ph; NH; S; 2-Cl; H; H; Me;
2-Cl-Ph; NH; S; 2-Cl; H; H; Me;
2-F-Ph; NH; S; 2-Cl; H; H; Me;
2-Et-Ph; NH; S; 2-Cl; H; H; Me;
2-PhO-Ph; NH; S; 2-Cl; H; H; Me;
2-Pr-Ph; NH; S; 2-Cl; H; H; Me;
2-Br-Ph; NH; S; 2-Cl; H; H; Me;
2-EtOC(O)-Ph; NH; S; 2-Cl; H; H; Me;
2-MeS-Ph; NH; S; 2-Cl; H; H; Me;
2-$NO_2$-Ph; NH; S; 2-Cl; H; H; Me;
2-MeO-5-Cl-Ph; NH; S; 2-Cl; H; H; Me;
2,4-(MeO)-Ph; NH; S; 2-Cl; H; H; Me;
2-Cl-5-$F_3$C-Ph; NH; S; 2-Cl; H; H; Me;
2-Me-5-Cl-Ph; NH; S; 2-Cl; H; H; Me;
2,3-Cl-Ph; NH; S; 2-Cl; H; H; Me;
2,5-Me-Ph; NH; S; 2-Cl; H; H; Me;
2,5-Cl-Ph; NH; S; 2-Cl; H; H; Me;
2-Me-5-F-Ph; NH; S; 2-Cl; H; H; Me;
2-$F_3$C-4-Br-Ph; NH; S; 2-Cl; H; H; Me;
2-$NO_2$-4-MeO-Ph; NH; S; 2-Cl; H; H; Me;
2-$NO_2$-4-Me-Ph; NH; S; 2-Cl; H; H; Me;
2-MeO-4-$NO_2$-Ph; NH; S; 2-Cl; H; H; Me;
2,5-Br-Ph; NH; S; 2-Cl; H; H; Me;
2-Cl-5-$NO_2$-Ph; NH; S; 2-Cl; H; H; Me;
2-$F_3$C-Ph; NH; S; 2-Cl; H; H; Pr;
2-$F_3$C-Ph; NH; S; 2-Cl; H; H; Bu;
2-$F_3$C-Ph; NH; S; H; H; H; Me;
2-$F_3$C-Ph; NH; S; 2-Cl; H; H; Ph;
2-$NO_2$-4-MeO-Ph; NH; S; 2-Cl; H; H; Pr;
2-$NO_2$-4-MeO-Ph; NH; S; 2-Cl; H; H; Bu;
2-MeS$O_2$-Ph; NH; S; 2-Cl; H; H; Me;
2-$F_3$C-4-Cl-Ph; NH; S; 2-Cl; H; H; Me; 2-$NO_2$-4-MeO-Ph; NH; S; 4-Cl; H; H; Bz;
2-$F_3$C-Ph; NH; S; 4-Cl; H; H; Me;
2-$NO_2$-4-MeO-Ph; NH; S; 2-Cl; H; H; pentyl;
2-$NO_2$-4-MeO-Ph; NH; S; 2-Cl; H; H; hexyl;
2-$NO_2$-4-MeO-Ph; NH; S; 3-Cl; H; H; Bz;
2-$NO_2$-4-F-Ph; NH; S; 2-Cl; H; H; Me;
2-$NO_2$-4-NC-Ph; NH; S; 2-Cl; H; H; Me;
2-$NO_2$-4-MeO-Ph; NH; S; 2-Cl; H; H; 1-naphthyl-methyl;
2-$NO_2$-4-MeO-Ph; NH; S; 2-Cl; H; H; 3-indolyl-methyl;
2-MeS-5-$F_3$C-Ph; NH; S; 2-Cl; H; H; Me;
2-$NO_2$-4-MeO-Ph; NH; S; 3-Cl; H; H; Me;
2-$NO_2$-5-Cl-Ph; NH; S; 2-Cl; H; H; Me;
2-$NO_2$-5-Me-Ph; NH; S; 2-Cl; H; H; Me;
2-$NO_2$-4-EtO-Ph; NH; S; 2-Cl; H; H; Me;
2-$NO_2$-4-MeO-Ph; NH; S; 2-Cl; H; H; 4-MeO-Bz;
2-$NO_2$-4-Cl-Ph; NH; S; 2-Cl; H; H; Me;
2-Br-4-Me-Ph; NH; S; 2-Cl; H; H; Me;
2-$NO_2$-4-MeO-Ph; NH; S; 2-Cl; H; H; 4-HO-Bz;
2-$F_3$C-4-$NO_2$-Ph; NH; S; 2-Cl; H; H; Me;
2-$NO_2$-4-MeO-Ph; NH; S; H; H; H; Bz;
2-$NO_2$-4-MeO-Ph; NH; S; 2-Cl; H; H; Ph-$C_2H_4$;
2-$NO_2$-4-MeO-Ph; NH; S; 2-Cl; H; H; EtO$C_2H_4$;
3-$NO_2$-2-pyridyl; NH; S; 2-Cl; H; H; Me;
2-$F_3$C-Ph; -; O; 2-Cl; H; H; Me;
Ph; -; S; 2-Cl; H; H; Me;
2-$NO_2$-4-MeO-Ph; NH; S; 4-Cl; H; H; Me;
2-$NO_2$-Ph; $CH_2$; S; 2-Cl; H; H; Me;
2-$NO_2$-4-MeO-Ph; NH; S; 2-MeO; H; H; Bu;
2-$NO_2$-4-MeO-Ph; NH; S; 2-MeO; H; H; Bz;
2-$NO_2$-4-MeO-Ph; NH; S; 2-Me; H; H; Bu;
2-$NO_2$-4-MeO-Ph; NH; S; 2-Me; H; H; Bz;
2-$NO_2$-4-MeO-Ph; NH; S; 2-Cl; H; H; Ph-Ph;
2-$NO_2$-4-MeO-Ph; NH; S; 2-Cl; H; H; cyclohexylmethyl;
2-$NO_2$-4-MeO-Ph; NH; S; 2-Cl; H; H; $(Me)_2NC_2H_4$;
2-$NO_2$-4-MeO-Ph; NH; S; 2-Cl; H; H; 3-HO-Bz;
Ph; S; S; 2-Cl; H; H; Me;
2-$NO_2$-4-MeO-Ph; NH; S; 2-Cl; H; H; heptyl.

5. A composition for treating acromegalia, hypophyseal adenomas and endocrinic gastroenteropancreatic tumors comprising an amount of a compound of the formula

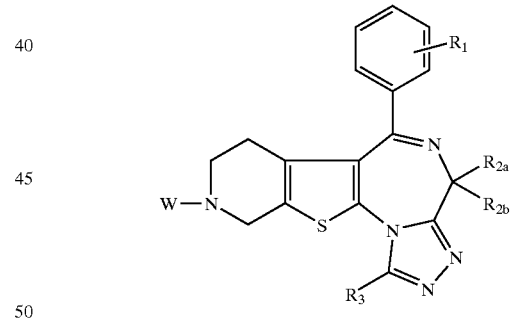

wherein W is hydrogen or

R is unsubstituted or substituted aryl or heteroaryl with at least one substituent selected from the group consisting of lower alkyl, lower alkoxy, lowr alkylthio, lower alkoxycarbonyl, lower alkylsulfonyl, halogen, —$CF_3$, —$OCF_3$, —OH, —$NO_2$, —CN, aryl, aryloxy, cycloalkyl and heterocycloalkyl, X is —$(CH_2)_n$—Z, Z is selected from the group consisting of a covalent bond, —NH, —O— and —S—, n is 0, 1 or 2, Y is oxygen or sulfur, $R_1$ is selected from the group consisting of hydrogen, —OH, halogen, lower alkyl and lower alkoxy, the alkyl and alkoxy being unsubstituted or substituted with at least one member of the group consisting of —CF$_3$, lower alkoxy, —NH$_2$ and mono and di-lower alkylamino, R$_{2a}$ and R$_{2b}$ are individually hydrogen or methyl, R$_3$ is selected from the group consisting of hydrogen, halogen, —NO$_2$, —CN, unsubstituted or substituted alkyl of 1 to 10 carbon atoms, unsubstituted or substituted lower alkenyl, unsubstituted or substituted alkynyl, unsubstituted or substituted cycloalkyl, unsubstituted or substituted cycloalkylalkyl, unsubstituted or substituted aryl, unsubstituted or substituted aralkyl, unsubstituted or substituted lower alkoxyalkyl, unsubstituted or substituted heteroaryl, unsubstituted or substituted heteroarylalkyl and —Z$_{31}$R$_{31}$, the substituents being selected from the group consisting of halogen, aryl, and

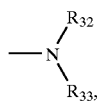

and —Z$_{32}$—R$_{34}$, Z$_{31}$ is selected from the group consisting of —O—, —C(O)—, —OC(O)— and —S—, R$_{31}$ is selected from the group consisting of hydrogen, lower alkyl, aryl and lower aralkyl, R$_{32}$ and R$_{33}$ are individually selected from the group consisting of hydrogen, lower alkyl, aralkyl and alkylcarbonyl or together with the nitrogen from a heterocycloalkyl, Z$_{33}$ is selected from the group consisting of oxygen, sulfur, —C(O)—, —S(O)—, —O—CO— and —SO$_2$—, R$_{34}$ is selected from the group consisting of hydrogen, lower alkyl, aryl and lower aralkyl and its non-toxic pharmaceutically acceptable salts sufficient to treat acromegalia, hypophyseal adenomas and endocrinic gastroenteropancreatic tumors and an inert pharmaceutical carrier.

6. A compound of the formula

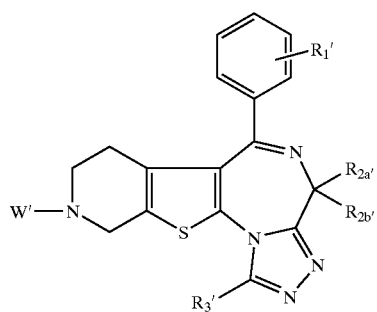

II wherein W' is R'—X'—C(Y)— and the substituents R', X', Y', R'$_1$, R$_{2a}$', R$_{2b}$' and R'$_3$ are respectively selected from the group consisting of:

2-F$_3$C-Ph: CH$_2$; O; 2-Cl; H; H; Me;
2-F$_3$C-Ph; CH$_2$; S; 2-Cl; H; H; Me;
2-F$_3$C-Ph; NH; O; 2-Cl; H; H; Me;
2-F$_3$C-Ph; CH$_2$NH; S; 2-Cl; H; H; Me;
Ph; O; O; 2-Cl; H; H; Me;
2-F$_3$C-Ph; NH; S; 2-Cl; Me; H; Me;
2-F$_3$C-Ph; NH; S; 2-Cl; H; H; Bz;
3-F$_3$C-Ph; NH; O; 2-Cl; H; H; Me;
2-NC-Ph; NH; S; 2-Cl; H; H; Me;
2-F$_3$C-Ph; NH; S; 2-Cl; H; H; Et;
2-F$_3$C-Ph; NH; S; 2-Cl; H; H; H;
2-terBu-Ph; NH; S; 2-Cl; H; H; Me;
1-naphthyl; NH; S; 2-Cl; H; H; Me;
2-Ph-Ph; NH; S; 2-Cl; H; H; Me;
2-F$_3$CO-Ph; NH; S; 2-Cl; H; H; Me;
2-Cl-Ph; NH; S; 2-Cl; H; H; Me;
2-F-Ph; NH; S; 2-Cl; H; H; Me;
2-Et-Ph; NH; S; 2-Cl; H; H; Me;
2-PhO-Ph; NH; S; 2-Cl; H; H; Me;
2-Pr-Ph; NH; S; 2-Cl; H; H; Me;
2-EtO-Ph; NH; S; 2-Cl; H; H; Me;
Ph; NH; S; 2-Cl; H; H; Me;
2-Br-Ph; NH; S; 2-Cl; H; H; Me;
2-EtOC(O)-Ph; NH; S; 2-Cl; H; H; Me;
2-MeS-Ph; NH; S; 2-Cl; H; H; Me;
2-morpholino-Ph; NH; S; 2-Cl; H; H; Me;
2-NO$_2$-Ph; NH; S; 2-Cl; H; H; Me;
2,6-isoPr-Ph; NH; S; 2-Cl; H; H; Me;
2,6-Me-Ph; NH; S; 2-Cl; H; H; Me;
2,5-(MeO)-Ph; NH; O; 2-Cl; H; H; Me;
2-MeO-5-Cl-Ph; NH; S; 2-Cl; H; H; Me;
2,4-(MeO)-Ph; NH; S; 2-Cl; H; H; Me;
2-Cl-5-F$_3$C-Ph; NH; S; 2-Cl; H; H; Me;
2-Me-5-Cl-Ph; NH; S; 2-Cl; H; H; Me;
2,3-Cl-Ph; NH; S; 2-Cl; H; H; Me;
2,5-Me-Ph; NH; S; 2-Cl; H; H; Me;
2,5-Cl-Ph; NH; S; 2-Cl; H; H; Me;
2-Cl-4-Me-Ph; NH; S; 2-Cl; H; H; Me;
2-Me-3-Cl-Ph; NH; S; 2-Cl; H; H; Me;
2-Me-5-F-Ph; NH; S; 2-Cl; H; H; Me;
2,3-Me-Ph; NH; S; 2-Cl; H; H; Me;
2-F$_3$C-4-Br-Ph; NH; S; 2-Cl; H; H; Me;
2-NO$_2$-4-MeO-Ph; NH; S; 2-Cl; H; H; Me;
2-NO$_2$-4-Me-Ph; NH; S; 2-Cl; H; H; Me;
2-MeO-4-NO$_2$-Ph; NH; S; 2-Cl; H; H; Me;
2,5-Br-Ph; NH; S; 2-Cl; H; H; Me;
2-MeO-5-NO$_2$-Ph; NH; S; 2-Cl; H; H; Me;
2-Cl-4-NO$_2$-Ph; NH; S; 2-Cl; H; H; Me;
2-Cl-5-NO$_2$-Ph; NH; S; 2-Cl; H; H; Me;
2-F$_3$C-Ph; NH; S; 2-Cl; H; H; Pr;
2-F$_3$C-Ph; NH; S; 2-Cl; H; H; Bu;
3-Ph-6-MeO-Ph; NH; S; 2-Cl; H; H; Me;
2-F$_3$C-Ph; NH; S; H; H; H; Me;
2-F$_3$C-Ph; NH; S; 2-Cl; H; H; Ph;
2-NO$_2$-4-MeO-Ph; NH; S; 2-Cl; H; H; Pr;
2-NO$_2$-4-MeO-Ph; NH; S; 2-Cl; H; H; Bu;
2-NO$_2$-4-F$_3$C-Ph; NH; S; 2-Cl; H; H; Me;
2-MeSO$_2$-Ph; NH; S; 2-Cl; H; H; Me;
2-F$_3$C-4-Cl-Ph; NH; S; 2-Cl; H; H; Me;
2-NO$_2$-4-MeO-Ph; NH; S; 4-Cl; H; H; Bz;
2-F$_3$C-Ph; NH; S; 4-Cl; H; H; Me;
2-NO$_2$-4-MeO-Ph; NH; S; 2-Cl; H; H; pentyl;
2-NO$_2$-4-MeO-Ph; NH; S; 2-Cl; H; H; hexyl;
3,5-F$_3$C-Ph; NH; S; 2-Cl; H; H; Me;
2-NO$_2$-4-MeO-Ph; NH; S; 3-Cl; H; H; Bz;
2-NO$_2$-4-F-Ph; NH; S; 2-Cl; H; H; Me;
2-NO$_2$-4-NC-Ph; NH; S; 2-Cl; H; H; Me;
2-NO$_2$-4-MeO-Ph; NH; S; 2-Cl; H; H; 1-naphthyl-methyl;
2-NO$_2$-4-MeO-Ph; NH; S; 2-Cl; H; H; 3-indolyl-methyl;
2-MeS-5-F$_3$C-Ph; NH; S; 2-Cl; H; H; Me;
2-NO$_2$-4-MeO-Ph; NH; S; 3-Cl; H; H; Me;
2-NO$_2$-4-MeO-Ph; NH; S; 2-Cl; H; H; Me;
2-NO$_2$-4-HO-Ph; NH; S; 2-Cl; H; H; Me;
2-NO$_2$-5-Cl-Ph; NH; S; 2-Cl; H; H; Me;
2-NO$_2$-5-Me-Ph; NH; S; 2-Cl; H; H; Me;
2-NO$_2$-4-EtO-Ph; NH; S; 2-Cl; H; H; Me;
2-NO$_2$-4-MeO-Ph; NH; S; 2-Cl; H; H; 4-MeO-Bz;
2-NO$_2$-4-Cl-Ph; NH; S; 2-Cl; H; H; Me;

2-Br-4-Me-Ph; NH; S; 2-Cl; H; H; Me;
2-NO$_2$-4-MeO-Ph; NH; S; 2-Cl; H; H; 4-HO-Bz;
2-F$_3$C-4-NO$_2$-Ph; NH; S; 2-Cl; H; H; Me;
2-NO$_2$-4-MeO-Ph; NH; S; H; H; H; Bz;
2-NO$_2$-4-MeO-Ph; NH; S; 2-Cl; H; H; Ph-C$_2$H$_4$;
2-NO$_2$-4-MeO-Ph; NH; S; 2-Cl; H; H; EtOC$_2$H$_4$;
3-NO$_2$-2-pyridinyl; NH; S; 2-Cl; H; H; Me;
4-MeO-Ph; CH$_2$; O; 2-Cl; H; H; Me;
2-indolyl; O; 2-Cl; H; H; Me;
3-indolyl; CH$_2$; O; 2-Cl; H; H; Me;
4-HO-Ph; C$_2$H$_4$; O; 2-Cl; H; H; Me;
4-HO-Ph; CH$_2$; O; 2-Cl; H; H; Me;
Ph; -; S; 2-Cl; H; H; Me;
5-MeO-2-indolyl; -; S; 2-Cl; H; H; Me;
2-NO$_2$-Ph; CH$_2$; O; 2-Cl; H; H; Me;
2-F$_3$C-Ph; CH$_2$; S; 2-Cl; H; H; Me;
2-NO$_2$-4-MeO-Ph; NH; S; 4-Cl; H; H; Me;
2-NO$_2$-Ph; CH$_2$; S; 2-Cl; H; H; Me;
2-NO$_2$-4-MeO-Ph; NH; S; 2-MeO; H; H; Bu;
2-NO$_2$-4-MeO-Ph; NH; S; 2-MeO; H; H; Bz;
2-NO$_2$-4-MeO-Ph; NH; S; 2-Me; H; H; Bu;
2-NO$_2$-4-MeO-Ph; NH; S; 2-Me; H; H; Bz;
2-NO$_2$-4-MeO-Ph; NH; S; 2-Cl; H; H; Ph-Ph;
2-NO$_2$-4-MeO-Ph; NH; S; 2-Cl; H; H; cyclohexyl methyl;
2-NO$_2$-4-MeO-Ph; NH; S; 2-Cl; H; H; 3-HO-Bz;
2-pyridinyl; NH; S; 2-Cl; H; H; Me;
Ph; S; S; 2-Cl; H; H; Me;
Ph; O; S; 2-Cl; H; H; Me;
2-NO$_2$-4-MeO-Ph; NH; S; 2-Cl; H; H; heptyl,
and the compounds of formula II wherein W' is hydrogen and substituents R'$_1$, R$_{2a}$', R$_{2b}$' and R'$_3$ are respectively selected from the group consisting of:

2-Cl; H; H; butyl;
2-Cl; H; H; benzyl;
2-Cl; H: H;
2-Cl; H; H; ethyl;
2-Cl; H; H; propyl;
2-Cl; H; H; Ph;
2-Cl; H; H; pentyl;
2-Cl; H; H; hexyl;
2-Cl; H; H; 4-HO-Bz;
2-Cl; H; H; 4-MeO-Bz;
2-Cl; H; H; 1-naphthyl-methyl;
2-Cl; H; H; 3-indolyl-methyl;
2-Cl; H; H; Ph-C$_2$H$_4$;
2-Cl; H; H; Ph-Ph;
2-Cl; H; H; EtOC$_2$H$_4$;
2-Cl; H; H; cyclohexylmethyl;
2-Cl; H; H; 3-OH-Bz;
2-Cl; H; H; (Me)$_2$NC$_2$H$_4$;
H; H; H; Me;
4-Cl; H; H; Bz;
H; H; H; Bz;
4-Cl; H; H; Me;
3-Cl; H; H; benzyl;
3-Cl; H; H; Me;
2-Me; H; H; butyl;
2-Me; H; H; benzyl;
2-MeO; H; H; butyl;
2-Cl; H; H; heptyl;
2-Cl; H; H; hexyl; and
2-Cl; H; H; pentyl.

* * * * *